United States Patent
Shelton, IV et al.

(10) Patent No.: US 9,795,380 B2
(45) Date of Patent: Oct. 24, 2017

(54) DEVICES AND METHODS FOR FACILITATING CLOSING AND CLAMPING OF AN END EFFECTOR OF A SURGICAL DEVICE

(71) Applicant: Ethicon Endo-Surgery, Inc., Cincinnati, OH (US)

(72) Inventors: Frederick E. Shelton, IV, Hillsboro, OH (US); Jerome R. Morgan, Cincinnati, OH (US); Emily A. Schellin, Cincinnati, OH (US); Jeffrey S. Swayze, Hamilton, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 370 days.

(21) Appl. No.: 14/474,750

(22) Filed: Sep. 2, 2014

(65) Prior Publication Data

US 2016/0058439 A1 Mar. 3, 2016

(51) Int. Cl.
| | | |
|---|---|---|
| *A61B 17/10* | (2006.01) | |
| *A61B 17/04* | (2006.01) | |
| *A61B 17/068* | (2006.01) | |
| *A61B 17/072* | (2006.01) | |
| *A61B 17/29* | (2006.01) | |
| *A61B 90/00* | (2016.01) | |

(52) U.S. Cl.
CPC ...... *A61B 17/068* (2013.01); *A61B 17/07207* (2013.01); *A61B 17/105* (2013.01); *A61B 2017/0725* (2013.01); *A61B 2017/07214* (2013.01); *A61B 2017/2912* (2013.01); *A61B 2017/2913* (2013.01); *A61B 2017/2917* (2013.01); *A61B 2017/2927* (2013.01); *A61B 2017/2933* (2013.01); *A61B 2017/2936* (2013.01); *A61B 2017/2941* (2013.01); *A61B 2090/037* (2016.02)

(58) Field of Classification Search
CPC .... A61B 2017/2913; A61B 2017/2933; A61B 17/068; A61B 17/105
USPC ............... 227/175.1–182.1; 606/139, 219
See application file for complete search history.

(56) References Cited

U.S. PATENT DOCUMENTS

| | | | | |
|---|---|---|---|---|
| 4,712,545 A | * | 12/1987 | Honkanen | A61B 17/1608 600/564 |
| 4,854,626 A | * | 8/1989 | Duke | B25J 1/04 294/104 |
| 5,304,185 A | * | 4/1994 | Taylor | A61B 17/0469 606/147 |
| 5,465,895 A | | 11/1995 | Knodel et al. | |

(Continued)

OTHER PUBLICATIONS

"MicroCutter XCHANGE™ 30." Inservice Poster. (Oct. 13).

(Continued)

*Primary Examiner* — Robert Long
(74) *Attorney, Agent, or Firm* — Mintz Levin Cohn Ferris Glovsky and Popeo, P.C.

(57) ABSTRACT

Devices and methods are provided for facilitating closing and clamping of an end effector of a surgical device. In general, the devices and methods can be configured to increase a moment arm of the end effector, thereby increasing a closure force of the end effector. In an exemplary embodiment, a surgical device can include a closure mechanism configured to provide an increased moment arm at the device's end effector, such as at a proximal end thereof.

11 Claims, 15 Drawing Sheets

(56) References Cited

U.S. PATENT DOCUMENTS

| | | | |
|---|---|---|---|
| 5,507,773 A * | 4/1996 | Huitema | A61B 17/07207 600/564 |
| 5,569,298 A * | 10/1996 | Schnell | A61B 17/29 606/174 |
| 5,725,536 A | 3/1998 | Oberlin et al. | |
| 6,206,903 B1 * | 3/2001 | Ramans | A61B 17/29 606/205 |
| 6,554,844 B2 * | 4/2003 | Lee | A61B 5/0084 606/1 |
| 6,582,451 B1 * | 6/2003 | Marucci | A61B 17/29 606/207 |
| 7,000,818 B2 | 2/2006 | Shelton, IV et al. | |
| 7,097,650 B2 * | 8/2006 | Weller | A61B 17/07207 227/175.1 |
| 7,473,258 B2 | 1/2009 | Clauson et al. | |
| 7,533,790 B1 | 5/2009 | Knodel et al. | |
| 7,641,671 B2 | 1/2010 | Crainich | |
| 7,669,746 B2 | 3/2010 | Shelton, IV | |
| 7,678,121 B1 | 3/2010 | Knodel | |
| 7,753,250 B2 | 7/2010 | Clauson et al. | |
| 7,918,376 B1 | 4/2011 | Knodel et al. | |
| 7,954,683 B1 | 6/2011 | Knodel et al. | |
| 7,963,432 B2 | 6/2011 | Knodel et al. | |
| 7,988,026 B2 | 8/2011 | Knodel et al. | |
| 8,056,789 B1 | 11/2011 | White et al. | |
| 8,066,720 B2 | 11/2011 | Knodel et al. | |
| 8,070,034 B1 | 12/2011 | Knodel | |
| 8,070,036 B1 | 12/2011 | Knodel | |
| 8,087,562 B1 | 1/2012 | Manoux et al. | |
| 8,123,795 B1 | 2/2012 | Knodel et al. | |
| 8,261,958 B1 | 9/2012 | Knodel | |
| 8,272,551 B2 | 9/2012 | Knodel et al. | |
| 8,317,071 B1 | 11/2012 | Knodel | |
| 8,317,072 B1 | 11/2012 | Knodel et al. | |
| 8,348,127 B2 * | 1/2013 | Marczyk | A61B 17/07207 227/177.1 |
| 8,356,740 B1 | 1/2013 | Knodel | |
| 8,357,174 B2 | 1/2013 | Roth et al. | |
| 8,365,973 B1 | 2/2013 | White et al. | |
| 8,403,956 B1 | 3/2013 | Thompson et al. | |
| 8,439,245 B2 | 5/2013 | Knodel et al. | |
| 8,439,246 B1 | 5/2013 | Knodel | |
| 8,496,155 B2 | 7/2013 | Knodel | |
| 8,505,800 B1 | 8/2013 | Knodel et al. | |
| 8,535,311 B2 * | 9/2013 | Schall | A61B 18/1445 606/51 |
| 8,556,153 B1 | 10/2013 | Knodel | |
| 8,617,203 B2 * | 12/2013 | Stefanchik | A61B 17/29 606/207 |
| 8,631,992 B1 | 1/2014 | Hausen et al. | |
| 8,636,189 B1 | 1/2014 | Knodel et al. | |
| 8,672,209 B2 * | 3/2014 | Crainich | A61B 17/07207 227/178.1 |
| 8,679,155 B2 | 3/2014 | Knodel et al. | |
| 8,690,909 B2 * | 4/2014 | Slater | A61B 17/295 606/207 |
| 8,701,960 B1 | 4/2014 | Manoux et al. | |
| 8,783,542 B2 * | 7/2014 | Riestenberg | A61B 90/92 227/176.1 |
| 9,204,877 B2 * | 12/2015 | Whitman | A61B 17/07207 |
| 2005/0101991 A1 * | 5/2005 | Ahlberg | A61B 17/282 606/205 |
| 2006/0053563 A1 * | 3/2006 | Skinner | B25B 7/10 7/127 |
| 2007/0162056 A1 * | 7/2007 | Gerbi | A61B 17/07207 606/153 |
| 2009/0065552 A1 | 3/2009 | Knodel et al. | |
| 2010/0069935 A1 * | 3/2010 | Crainich | A61B 17/12 606/157 |
| 2010/0155453 A1 | 6/2010 | Bombard et al. | |
| 2011/0204120 A1 | 8/2011 | Crainich | |
| 2012/0010652 A1 | 1/2012 | Hahnen et al. | |
| 2012/0150176 A1 * | 6/2012 | Weizman | A61B 17/07207 606/45 |
| 2012/0248169 A1 | 10/2012 | Widenhouse et al. | |
| 2013/0112730 A1 * | 5/2013 | Whitman | A61B 17/07207 227/175.1 |
| 2013/0277410 A1 | 10/2013 | Fernandez et al. | |
| 2014/0025070 A1 * | 1/2014 | Kerr | A61B 18/1445 606/45 |
| 2014/0041191 A1 | 2/2014 | Knodel | |
| 2014/0175146 A1 | 6/2014 | Knodel | |
| 2015/0048141 A1 * | 2/2015 | Felder | A61B 17/11 227/179.1 |
| 2016/0058441 A1 * | 3/2016 | Morgan | A61B 17/0644 606/219 |
| 2017/0119402 A1 * | 5/2017 | Heinemann | A61B 17/1608 |

OTHER PUBLICATIONS

"MicroCutter XCHANGE™ 30." Instructions for Use. (2014).
"MicroCutter XCHANGE® 30 Videos." Cardica. Web. May 7, 2014. http://www.cardica.com/inservice-guide.php.
"MicroCutter XCHANGE® 30: The World's First and Only Articulating 5mm Stapler." Cardica. Web. May 7, 2014. http://www.cardica.com/minimally-invasive-surgery.php.
U.S. Appl. No. 14/300,954, filed Jun. 10, 2014.
European Search Report for EP App. No. EP15183381.1 dated May 9, 2016.

* cited by examiner

US 9,795,380 B2

DEVICES AND METHODS FOR FACILITATING CLOSING AND CLAMPING OF AN END EFFECTOR OF A SURGICAL DEVICE

FIELD OF THE INVENTION

The present disclosure relates generally to facilitating closing and clamping of an end effector of a surgical device.

BACKGROUND

Minimally invasive surgical instruments are often preferred over traditional open surgical devices due to the reduced post-operative recovery time and minimal scarring associated with minimally invasive procedures. Laparoscopic surgery is one type of minimally invasive surgery (MIS) procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, stapler, clip applier, access device, drug/gene therapy delivery device, and energy device using ultrasound, radiofrequency, laser, etc.).

For example, staplers including end effectors for grasping tissue have been developed which secure tissue between two jaws. Staples contained in one of the jaws can be driven into the grasped tissue and deformed to hold the tissue by impinging on the other jaw. The staples can form a predetermined pattern (e.g., one or more lines of staples) based upon the configuration of the staples in the one of the jaws. The stapler can be a linear stapler, in which the predetermined pattern includes one or more longitudinal lines of staples. Though staplers can be effective to grasp and staple tissue, it can be difficult to grasp and/or staple the tissue based on a variety of factors, such as a size and/or shape of the staple, a thickness and/or toughness of the tissue, etc.

Some staplers can be refilled after firing staples. In some staplers, the staples can be contained in a cartridge which can be removable from the stapler's jaw to allow the stapler to be refilled with staples contained in another cartridge inserted into the jaw. However, this refilling of cartridges can be difficult since the cartridges can be relatively small and accordingly difficult to manipulate and/or properly secure within the jaw. Refilling a stapler with a new cartridge can thus be time consuming and/or can result in an improperly loaded cartridge that can misfire staples or otherwise function improperly during use on a patient.

Accordingly, there remains a need for improved methods and devices for stapling tissue.

SUMMARY

A surgical fastening device comprises an elongate shaft and an end effector coupled to a distal end of the elongate shaft. The end effector includes a cartridge jaw and an anvil pivotally coupled to one another at a pivot point, a cam pin disposed within a cam slot formed in each of the cartridge jaw and the anvil, and a closure mechanism proximal to the pivot point. The cam pin is slidable within the cam slots to move the anvil and cartridge jaw between a spaced-apart position and a closed position in which the cartridge jaw and the anvil are configured to engage tissue therebetween. Further, the closure mechanism is positioned adjacent to a proximal-most end of the anvil and is configured to apply a force to the proximal-most end of the anvil to compress tissue engaged between the anvil and the cartridge jaw.

The closure mechanism can be in the form of a lobe cam that rotates to apply a force to the proximal-most end of the anvil to move the proximal-most end of the anvil away from the cartridge jaw. The lobe cam can be rotatably disposed within the end effector.

In one aspect the fastening device further comprises a cable coupled to the lobe cam and configured to rotate the lobe cam to cause the lobe cam to apply a force to the proximal-most end of the anvil. The lobe cam can include a biasing element that biases the lobe cam to a position in which no force is applied to the proximal-most end of the anvil.

The closure mechanism can comprise a wedge configured to apply a force to the proximal-most end of the anvil to move the proximal-most end of the anvil away from the cartridge jaw. In one aspect the wedge is configured to advance distally to apply the force to the proximal-most end of the anvil. The wedge can be formed on a distal end of a pusher shaft slidably disposed through the elongate shaft.

According to another aspect, a surgical fastening device comprises a handle, an elongate shaft extending distally from the handle, and an end effector coupled to a distal end of the elongate shaft. The end effector can include first and second jaws pivotally coupled to one another and movable about a pivot point between an open position and a closed position for engaging tissue. The fastener also includes a lobe cam positioned proximal to the pivot point and between a proximal-most end of each of the first and second jaws. The lobe cam is rotatable to move the proximal-most ends of the first and second jaws apart to thereby move the first and second jaws to the closed position. In one aspect the lobe cam can be biased to a position in which the first and second jaws are in the open position, and rotation of the lobe cam overcomes the bias to move the first and second jaws to the closed position.

The surgical fastening device further comprises a cable coupled to the lobe cam and configured to rotate the lobe cam to cause the lobe cam to apply a force to move the first and second jaws to the closed position. The device can be constructed such that a distance between the first and second jaws at the pivot point is adjustable.

In yet another aspect, a surgical fastening device comprises a handle, an elongate shaft extending distally from the handle, and an end effector coupled to a distal end of the elongate shaft. The end effector includes first and second jaws pivotally coupled to one another and movable about a pivot point between an open position and a closed position for engaging tissue. The device further includes a two-bar linkage coupled to the first and second jaws and configured to apply a force to the proximal-most end of the first jaw to move the proximal-most end of the first jaw away from the proximal-most end of the second jaw.

The two-bar linkage can include a first bar coupled to an actuation shaft slidably disposed through the elongate shaft and a second bar coupled to the first bar and having a pin formed thereon, wherein the pin is slidably disposed within a slot formed in the second jaw. Further, the two-bar linkage is coupled to an actuation shaft that is pulled proximally to cause the two-bar linkage to apply the force to the first jaw.

A method for fastening tissue is also provided. The method comprises inserting an end effector into a body cavity of a patient's body, wherein the end effector being coupled to a distal end of an elongate shaft extending from a handle positioned outside of the patient's body, manipulating the handle of the surgical device to position tissue between a cartridge jaw and an anvil of the end effector, actuating a closure mechanism to advance a pin through cam slots formed in each of the cartridge jaw and the anvil to cause the cartridge jaw and the anvil to engage the tissue positioned therebetween, and actuating a compression mechanism to move a proximal-most end of each of the anvil and the cartridge jaw away from one another to further compress the tissue engaged therebetween.

In one aspect actuating the compression mechanism comprises rotating a lobe cam disposed between a proximal-most end of each of the anvil and the cartridge jaw. In another aspect actuating the compression mechanism comprises advancing a wedge distally along the elongate shaft and between the proximal-most end of each of the anvil and cartridge jaw. In yet another aspect actuating the compression mechanism comprises actuating a two-bar linkage mechanism coupled to the anvil and cartridge jaws.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Figure 1:
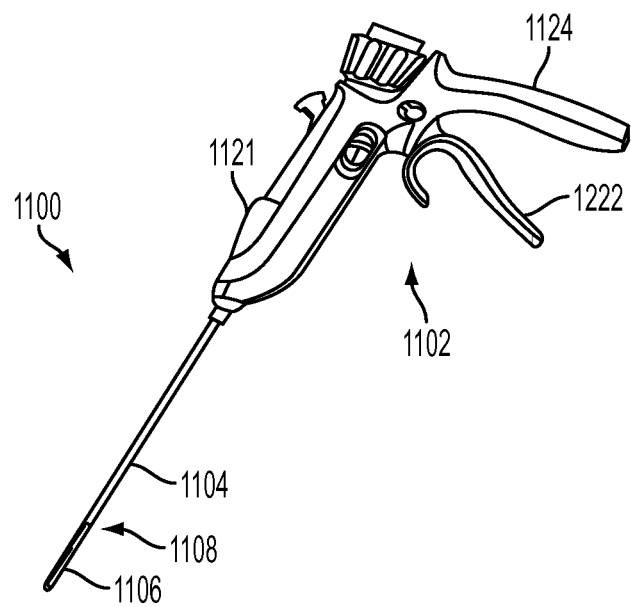
FIG. 1 is a perspective view of one embodiment of a surgical device configured to apply fasteners to tissue and including an end effector, the end effector being in a closed position.

FIG. 1 illustrates one embodiment of a surgical device 1100 that can be configured to apply staples to tissue. The device 1100 in this illustrated embodiment includes a linear stapler configured to apply linear rows of staples. Other embodiments of surgical devices that can be configured to apply staples to tissue are described in U.S. Pat. No. 5,465,895 entitled "Surgical Stapler Instrument" filed Feb. 3, 1994, U.S. Pat. No. 7,000,818 entitled "Surgical Stapling Instrument Having Separate Distinct Closing And Firing Systems" filed May 20, 2003, U.S. Pat. No. 7,669,746 entitled "Staple Cartridges For Forming Staples Having Differing Formed Staple Heights" filed on Aug. 31, 2005, and U.S. Pat. Pub. No. 2014/0175146 entitled "Microcutter Stapling Apparatus Clamp And Deploy Mechanisms Systems And Methods" filed Dec. 19, 2013, which are hereby incorporated by reference in their entireties.

Figure 2:
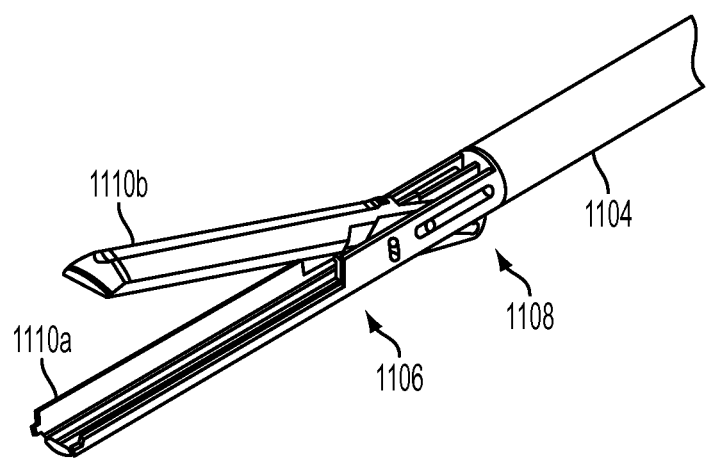
FIG. 2 is a perspective view of the end effector of FIG. 1 in an open position.
Figure 3:
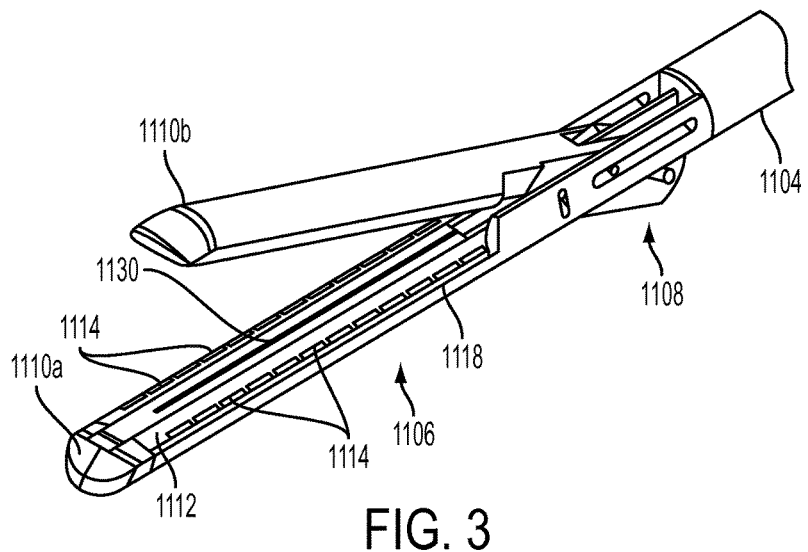
FIG. 3 is a perspective view of the end effector of FIG. 2 with one embodiment of a cartridge removably coupled thereto.

Referring again to FIG. 1, the device 1100 can include a proximal handle portion 1102 having an elongate shaft 1104 extending distally therefrom. As also shown in FIG. 2 and FIG. 3, the shaft 1104 can have an end effector 1106 coupled to a distal end thereof. The end effector 1106 can be coupled to the shaft 1104 at a pivot joint 1108. A proximal end of the end effector 1106 can be pivotally coupled to the joint 1108 at a distal end of the shaft 1104. The end effector 1106 in this illustrated embodiment includes a tissue grasper having a pair of opposed first and second jaws 1110a, 1110b configured to move between open and closed positions. The first jaw is also referred to herein as a "bottom jaw" and a "cartridge jaw," and the second jaw is also referred to herein as an "upper jaw" and an "anvil." As discussed further below, the handle portion 1102 can be configured to be manipulated to effect the opening and closing of the opposed jaws 1110a, 1110b, e.g., movement of one or both the jaws 1110a, 1110b about the pivot joint 1108, and the handle portion 1102 can be configured to be manipulated to effect the firing of staples (not shown) from a one of the jaws 1110a, 1110b, e.g., a bottom or cartridge one of the jaws 1110a. The staple firing can be independent of the opening and closing of the jaws 1110a, 1110b.

The handle portion 1102 can have a variety of sizes, shapes, and configurations. The handle portion 1102 can include a main housing 1121, which can house a variety of elements therein and can have some elements accessible outside thereof, such as a movable trigger 1122 and a stationary handle 1124. The movable trigger 1122 can be configured to be manually manipulated to move the movable trigger 1122 relative to the stationary handle 1124 so as to, e.g., effect closing of the jaws 1110a, 1110b.

The shaft 1104 can have a variety of sizes, shapes, and configurations. In an exemplary embodiment, the shaft 1104 can be rigid, e.g., made from a generally non-bendable material such as a metal (e.g., stainless steel, titanium, etc.) or a hard polymer. In other embodiments, the shaft 1104 can be configured to bend, such as being made from a generally flexible material, by including one or more articulation regions, etc. The shaft 1104 can have any longitudinal length, although in an exemplary embodiment it can be long enough to allow the handle portion 1102 to be manipulated outside a patient's body while the shaft 1104 extends through an opening in the body with the end effector 1106 disposed within a body cavity. In this way, the end effector 1106 can be easily manipulated when the device 1100 is in use during a surgical procedure. The shaft 1104 can have any diameter. For example, the shaft's diameter can be less than or equal to about 10 mm, e.g., less than or equal to about 7 mm, less than or equal to about 5 mm, etc., which can allow for insertion of the shaft 1104 through an minimally invasive access device, e.g., a trocar, a cannula, a multiport access device, etc., such as during a laparoscopic surgical procedure. The end effector 1106 coupled to the shaft's distal end can have a diameter equal to or less than the shaft's diameter, at least when the jaws 1110a, 1110b are in the closed position, which can facilitate insertion of the device's distal portion into a patient's body.

The end effector 1106 can have a variety of sizes, shapes, and configurations. In an exemplary embodiment, the end effector 1106 can be rigid. As shown in FIG. 2 and FIG. 3, the end effector 1106 including the first and second jaws 1110a, 1110b can be disposed at a distal end of the surgical device 1100. As in this illustrated embodiment, when the jaws 1110a, 1110b move between the open and closed positions, the second jaw 1110b can be configured to remain stationary relative to the shaft 1104, and the first jaw 1110a can be configured to move relative to the shaft 1104 and the second jaw 1110b by pivoting at the pivot joint 1108.

Figure 4:
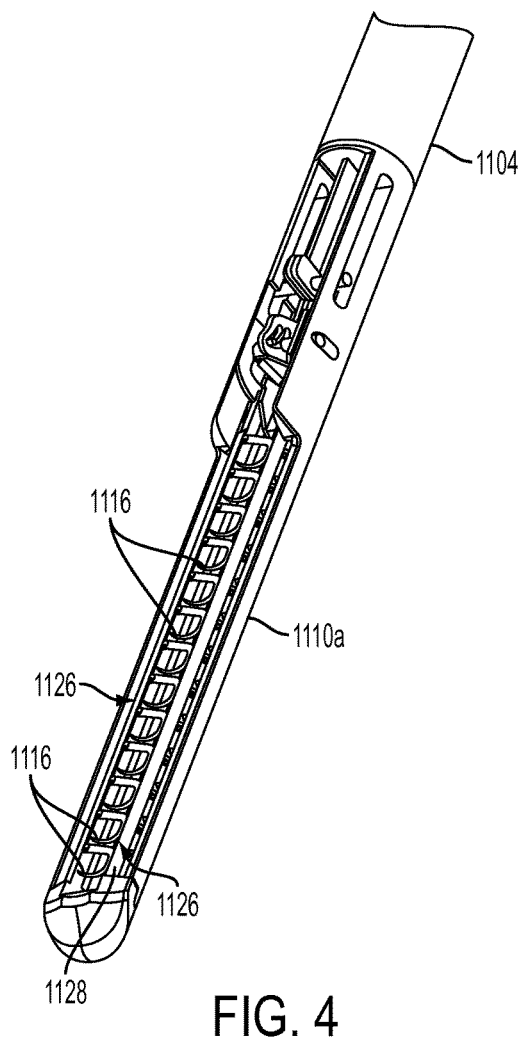
FIG. 4 is a perspective, partially cross-sectional view of the end effector and the cartridge of FIG. 3.

The end effector 1106 can be configured to releasably and replaceably seat a cartridge 1112 therein, as shown in FIG. 3 and FIG. 4. In this way, when the staples have been fired from the cartridge 1112, the cartridge 1112 can be removed from the second jaw 1110b and, optionally, replaced with another cartridge having another plurality of staples disposed therein. FIG. 2 shows the end effector 1106 without the cartridge 1112 seated therein. The end effector 1106 can be configured to receive the cartridge 1112 in the first jaw 1110a thereof, e.g., in a channel formed in the first jaw 1110a. The first jaw 1110a can be configured to seat cartridges of different sizes, thereby facilitating versatility of the device 1100.

Figure 5:
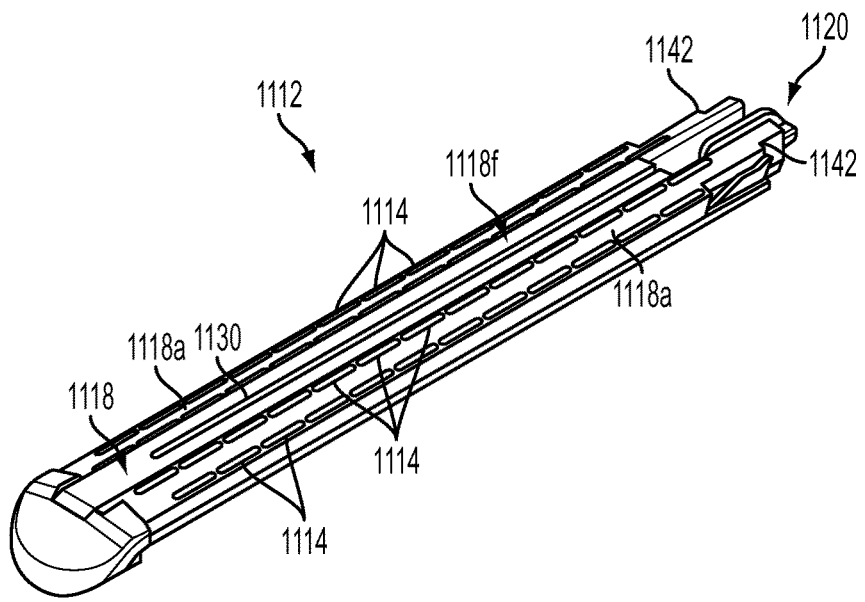
FIG. 5 is a perspective view of the cartridge of FIG. 3.
Figure 6:
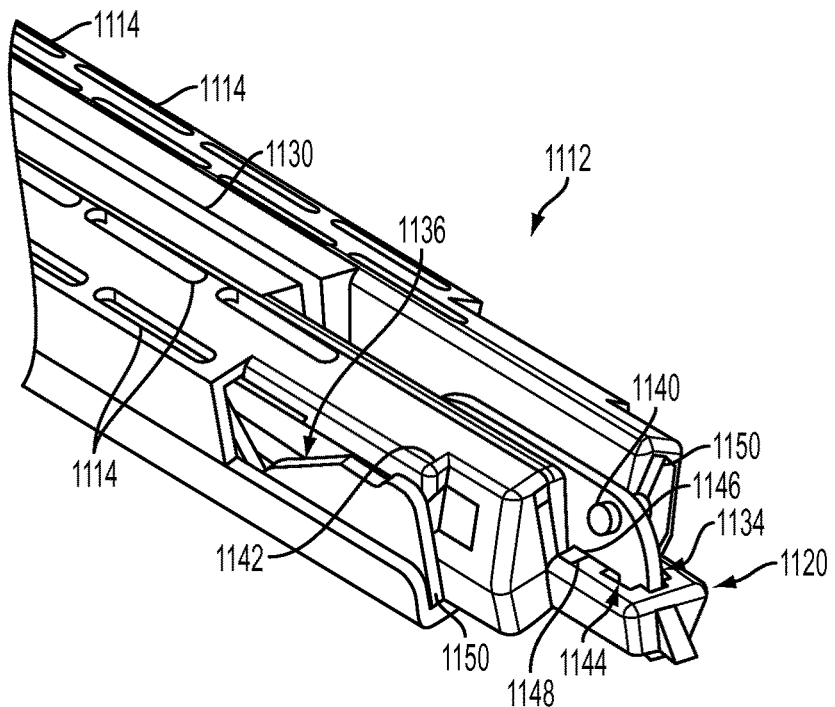
FIG. 6 is another perspective view of the cartridge of FIG. 3.
Figure 7:
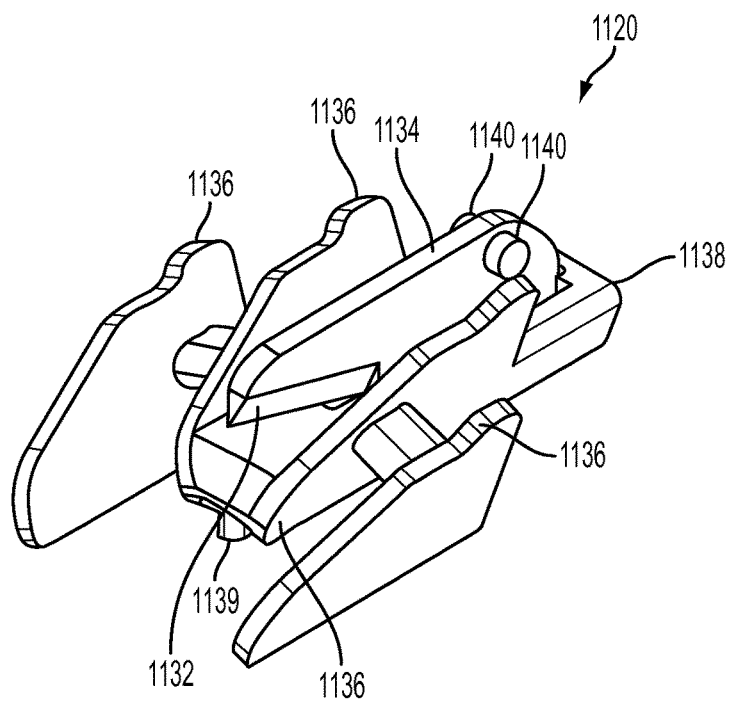
FIG. 7 is a perspective view of a sled of the cartridge of FIG. 3, the sled including a cutting element, and the cutting element being in a first position.
Figure 8:
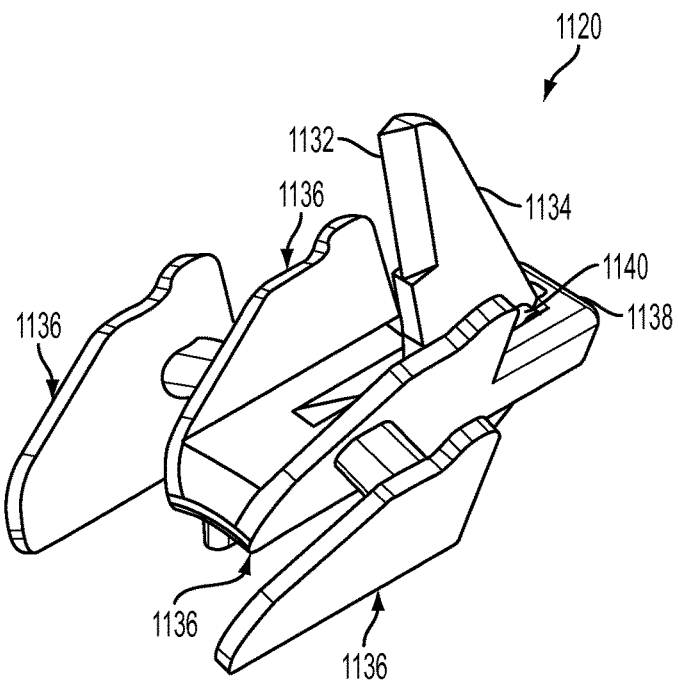
FIG. 8 is a perspective view of the sled of FIG. 7 with the cutting element in a second position that is different from the first position.

The cartridge 1112 can have a variety of sizes, shapes, and configurations, as will be appreciated by a person skilled in the art. As shown in FIG. 4, FIG. 5, and FIG. 6, the cartridge 1112 can include a sled 1120 and can have a plurality of staples 1116 disposed therein. The sled 1120 is also illustrated in FIG. 7 and FIG. 8. The cartridge 1112 can include a plurality openings 1114 formed in a tissue engaging surface 1118 thereof, as shown in FIG. 3, FIG. 5, and FIG. 6. The staples 1116 disposed in the cartridge 1112 can be configured to be ejected from the cartridge 1112 through the openings 1114, e.g., one staple 1116 out of each opening 1114 (as in this illustrated embodiment), two staples out of each opening 1114, etc. The openings 1114 can define staple-receiving recesses of the cartridge 1112 in which the staples 1116 are seated prior to being ejected from the cartridge 1112.

The staples 1116 can have a variety of sizes, shapes, and configurations. In this illustrated embodiment, the staples 1116 each have a D-shape and include a first leg that is substantially straight and a second leg that is curved. A person skilled in the art will appreciate that the first leg may not be precisely straight, e.g., due to manufacturing tolerances, but nevertheless be considered to be substantially straight. Each of the staples 1116 can be configured to be plastically deformable such that the staples 1116 can each be configured to change shape, such as when the staple 1116 is pressed against a tissue engaging surface (not shown) of the first jaw 1110a that faces the tissue engaging surface 1118 of the second jaw 1110b, while remaining a single unit, e.g., without either of the first and second legs breaking. A gap of space can exist between a terminal end of the first leg and a terminal end of the second leg. In other words, the "D" shape can have a gap therein. The gap of space can facilitate plastic deformation of the staple 1116.

The staples 1116 can each be frangibly attached to a carrier 1126, also referred to herein as a "carrier strip," disposed within the cartridge 1112. The staples 1116 can be frangibly attached to the carrier 1126 by, e.g., being stamped together with the carrier 1126 such that the staples 1116 and the carrier 1126 forms a single piece. The staples 1116 can each be configured to detach from the carrier 1126 when fired from the cartridge 1112. In some embodiments, some or all of the staples 1116 can be frangibly attached to another element, such as another element disposed within the cartridge 1112, an inner surface of the cartridge 1112, the tissue-engaging surface 1118 of the cartridge 1112, etc. The carrier 1126 can be fixedly attached to an upper surface of one or more rails 1128 defined by the cartridge 1112. The carrier 1126 can be configured to remain stationary relative to the cartridge 1112.

As shown in FIG. 3, FIG. 5, and FIG. 6, the cartridge 1112 can have a longitudinal slot 1130 formed therein. The longitudinal slot 1130 can extend along a substantially flat central portion 1118f of the tissue-engaging surface 1118. The slot 1130 can be configured to have a cutting element such as a knife (not shown) extend therethrough so as to be configured to cut tissue engaged by the tissue-engaging surface 1118, as discussed further below. The openings 1114 can be formed in angled portions 1118a of the tissue-engaging surface 1118 on both sides of the slot 1130, as shown in FIG. 3, FIG. 5, and FIG. 6. In some embodiments, the tissue-engaging surface 1118 can be substantially flat, e.g., not have angled portions, while in other embodiments, the tissue-engaging surface 1118 can be angled, e.g., not have any substantially flat portions.

As shown in FIG. 5 and FIG. 6, the cartridge 1112 can include a gap-setting feature 1142 configured to set of gap of space between the first and second jaws 1110a, 1110b when the jaws 1110a, 1110b are closed and the cartridge 1112 is seated in the second jaw 1110b. In this way, the gap-setting feature 1142 can be configured to define a minimum distance between the facing tissue-engaging surfaces of the first and second jaws 1110a, 1110b. The gap-setting feature 1142 can have a variety of sizes, shapes, and configurations. As in this illustrated embodiment, the gap-setting feature 1142 can include an indentation inward toward a lateral center of the cartridge 1112, where a portion of a lateral edge of the cartridge 1112 immediately proximal to the gap-setting feature 1142 is located laterally inward relative to a portion of a lateral edge of the cartridge 1112 located immediately distal to the gap-setting feature 1142.

The sled 1120 of the cartridge 1112 can have a variety of sizes, shapes, and configurations. The sled 1120 can be configured to translate longitudinally along the cartridge 1112 to cause deployment of the staples 1116 therefrom and to cause tissue engaged by the end effector 1106 to be cut with the cutting element extending through the slot 1130. The staples 1116 can be arranged longitudinally in the cartridge 1112, as shown in FIG. 4, and the sled 1120 can be configured to sequentially engage the longitudinally arranged staples 1116 as the sled 1120 translates longitudinally. As illustrated in FIG. 7 and FIG. 8, the sled 1120 can include a plurality of wedges 1136 and can include a cutting element 1134, which in this illustrated embodiment includes a knife with a blade 1132. The sled 1120 in this illustrated embodiment includes four wedges 1136 but the sled 1120 can include another number of wedges 1136 as appropriate for the arrangement of the staples 1116 in the cartridge 1112. Each of the wedges 1136 can have a shape configured to cause the staples 1116 contacted by that wedge 1136 to move upward toward the second jaw 1110b through the openings 1114 and deform against the second jaw 1110b. As shown in FIG. 6, the cartridge 1112 can include a plurality of longitudinal slots 1150 formed therein, each of the slots 1150 being configured to slidably receive one of the wedges 1136 therein. The slots 1150 can facilitate consistent, straight movement of the wedges 1136 through the cartridge 1112 to help ensure proper engagement of the wedges 1136 with the staples 1116.

Each of the wedges 1136 can be attached to a base 1138 of the sled 1120 and can be in a fixed position relative thereto. The base 1138 can have a guide element 1139 extending generally downward therefrom. The guide element 1139 can be configured to slide within a channel formed in the cartridge 1112 that includes the sled 1120. The cutting element 1134 can also be attached to the base 1138, but the cutting element 1134 can be configured to move relative to the base 1138. The cutting element 1134 can be substantially laterally centered in the base 1138, which can facilitate substantially central positioning of the cutting element 1134 relative to tissue engaged by the end effector 1106.

The cutting element 1134 can be configured to be movable relative to a remainder of the sled 1120 between a first position, shown in FIG. 7, and a second position, shown in FIG. 6 and FIG. 8. The first position can be an initial position of the cutting element 1134. In the first position, also referred to herein as a "stowed position," the blade 1132 can be generally obscured, e.g., oriented generally downward as shown in the embodiment of FIG. 4, FIG. 5, FIG. 6, and FIG. 7, which can help prevent the blade 1132 from inadvertent cutting, such as accidentally cutting a user of the device 1100 during seating of the cartridge 1120 within the end effector 1104 and/or premature cutting of tissue engaged by the end effector 1104. The base 1138 can have a cavity 1144 formed therein, as shown in FIG. 6, which can be configured to seat the cutting element 1134 at least partially therein when the cutting element 1134 is in the first position. In the second position, also referred to herein as an "upright position," the blade 1132 can be generally unobscured and facing a distal direction as shown in the embodiment of FIG. 6 and FIG. 8, which can allow the blade 1132 to extend through the slot 1130 and cut tissue engaged by the end effector 1106.

The sled 1120 can include a pivot member 1140 configured to facilitate movement of the cutting element 1134 relative to the remainder of the sled 1120. The pivot member 1140 can have a variety of sizes, shapes, and configurations. The pivot member 1140 can be attached to the cutting element 1134 such that engagement of the pivot member 1140 can cause the cutting element 1134 to pivot about a pivot point so as to move relative to the remainder of the sled. As in this illustrated embodiment the pivot member 1140 can include two separate pins extending laterally from opposite sides of the cutting element 1134. In other embodiments, the pivot member 1140 can include a single pin extending through the cutting element 1134 to extend laterally from opposite sides therefrom, a single pin extending laterally from one side of the cutting element 1134, etc. At the pivot point, the sled 1120 can include a pivot axle 1146 extending laterally from the cutting element 1134, and can include an axle cavity 1148 formed in the base 1138 and configured to receive the pivot axle 1146 therein.

The surgical devices described herein can be used in a variety of surgical procedures. In an exemplary embodiment, the procedure can be a minimally invasive procedure in which the surgical device can be advanced into a body of a patient through a relatively small opening in the patient. In a minimally invasive surgical procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. As will be appreciated by a person skilled in the art, the surgical device can be advanced into the patient's body in a variety of ways, such as by being inserted transorally therein, inserted through an introducer device, inserted through a scoping device, inserted directly through an incision, etc. Although the following embodiment of use of a surgical device in a surgical procedure is described with respect to the device 1100 of FIG. 1, any of the surgical devices described herein can be similarly used.

The surgical devices described herein can have any one or more variations to facilitate effective use of the device. Examples of such variations are described further below.

In some embodiments, a surgical device such as the above-mentioned surgical device 1100 can be configured to facilitate closing of an end effector and clamping of tissue by the end effector. In general, the surgical device can be configured to increase a moment arm of the end effector, thereby increasing a closure force of the end effector. The end effector can thus be more securely closed and can more securely grasp tissue. The tissue can therefore be less likely to shift position once grasped by the end effector, which can facilitate grasping of target tissue by the end effector and/or can allow fasteners to be fired more accurately into the tissue from the end effector. The increased moment arm can provide significantly higher end effector closure efficacy in response to an actuation force, e.g., manipulation of the device's handle to effect end effector closure, than in response to the same actuation force applied. The smaller a diameter of an elongate shaft of the device, the lower the load that an end effector at a distal end of the shaft can tolerate without breaking and/or other reduced effectiveness. By increasing a moment arm at the end effector's proximal end, the shaft can have a relatively small diameter, e.g., diameters appropriate for use of the device in a minimally invasive surgical procedure, while having an end effector that is relatively easy to close and while providing relatively strong clamping of tissue engaged by the end effector. In an exemplary embodiment, a surgical device can include a closure mechanism configured to provide an increased moment arm at the device's end effector, such as at a proximal end thereof.

Figure 9:
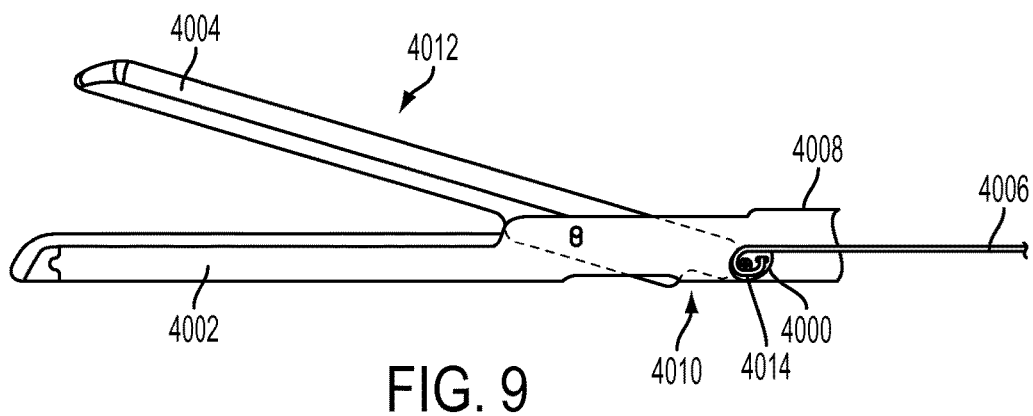
FIG. 9 is a side, partially transparent view of one embodiment of a surgical device including an end effector and a closure mechanism in the form of a lobe cam, the end effector being in an open position.

In some embodiments, a surgical device can include a closure mechanism in the form of a lobe cam. FIG. 9 illustrates one embodiment of a surgical device that includes a closure mechanism 4000 in the form of a lobe cam. In general, the lobe cam 4000 can be configured to improve closing of the device's end effector 4012 and clamping of tissue by the end effector 4012. The end effector 4012 can be coupled to a distal end of the device's elongate shaft 4008, and can include an upper jaw 4004 and a bottom jaw 4002. The lobe cam 4000 can be configured to be pulled in a proximal direction 4016 to improve the moment arm.

The lobe cam 4000 can have a variety of sizes, shapes, and configurations. As in this illustrated embodiment, the closure mechanism 4000 can be positioned adjacent a proximal end 4010 of the upper jaw 4004, as in this illustrated embodiment. The lobe cam 4000 can be pivotally coupled to the bottom jaw 4002 at a pivot point 4014 about which the lobe cam 4000 can be configured to move. The device can include an actuator 4006 configured to be actuated via manipulation of the device's handle (not shown) so as to move the closure mechanism 4000, as discussed further below. The actuator 4006 can extend along the shaft 4008, e.g., through an inner lumen thereof, and can be coupled to the closure mechanism 4000. The actuator 4006 includes a cable in this illustrated embodiment, but the actuator 4006 can have other sizes, shapes, and configurations.

Figure 10:
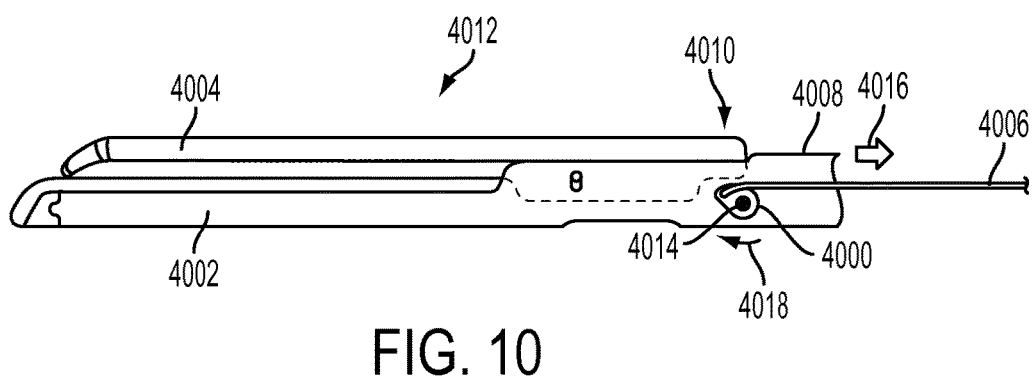
FIG. 10 is a side, partially transparent view of the device of FIG. 9, the end effector in an intermediate position between open position and a closed position.
Figure 11:
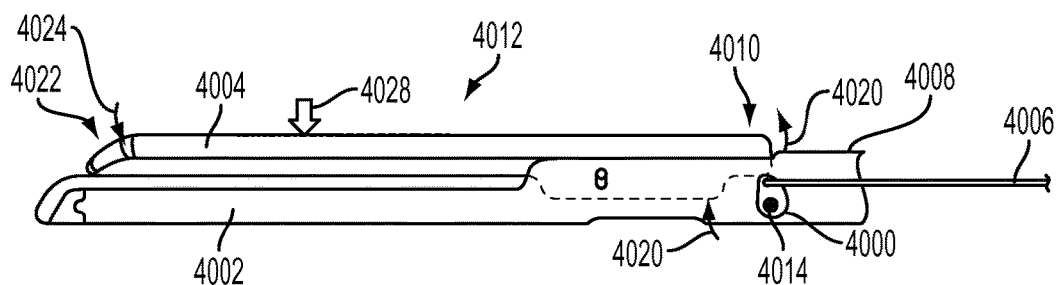
FIG. 11 is a side, partially transparent view of the device of FIG. 10, the end effector being in the closed position.

The lobe cam 4000 can be configured to move between first and second positions. The lobe cam 4000 can be in a first position when the end effector 4012 is in the open position, as shown in FIG. 9, and can be in the second position when the end effector 4012 is in the closed position, as shown in FIG. 11. FIG. 10 shows the lobe cam 4000 in an intermediate position between the first and second positions when the end effector 4012 is moving from the open position to the closed position. The lobe cam 4000 can be biased to the first position, e.g., by the actuator 4006 applying a biasing force thereto. In other embodiments, the lobe cam 4000 can be biased to the second position, e.g., by the actuator 4006 applying a biasing force thereto.

When the end effector 4012 begins to move from the open position of FIG. 9, the actuator 4006 can be pulled in the proximal direction 4016, as shown in FIG. 10. The pulling of the actuator 4006 can cause the lobe cam 4000 to rotate, as shown by an arrow 4018 in FIG. 10, thereby causing the lobe cam 4000 to push against the upper jaw 4004 so as to apply a force to the proximal end 4010 thereof. This force can increase closure of the end effector 4012. As the end effector 4012 continues closing, the lobe cam 4000 can continue applying the force to the upper jaw's proximal end 4010. When the end effector 4012 is in the closed position, as shown in FIG. 11, the lobe cam 4000 can continue applying the force to the upper jaw 4004, which can increase a clamping force of the end effector 4012 by forcing the upper jaw's proximal end in an upward direction 4020, thereby forcing the upper jaw's distal end 4022 in a downward direction 4024 toward the bottom jaw 4002. An end reaction force when the end effector 4012 is in the closed position can be in a direction 4028 that is substantially perpendicular to a longitudinal axis of the shaft 4008 along which the actuator 4006 extends and along which the actuator 4006 applies force to the lobe cam 4000. The end effector 4012 can thus be effectively closed and effectively clamp tissue engaged since substantially all of the pulling force in the proximal direction 4016 is applied to the end reaction force in the substantially perpendicular direction 4028. When the end effector 4012 moves from the closed position to the open position, the lobe cam 4000 can move from the second position back to the first position.

Figure 12:
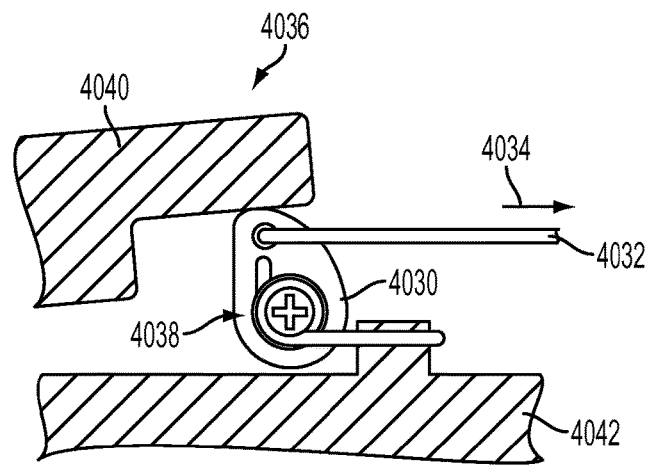
FIG. 12 is a side, partially cross-sectional view of another embodiment of a surgical device including an end effector and a closure mechanism in the form of a lobe cam, the end effector being in a closed position.
Figure 13:
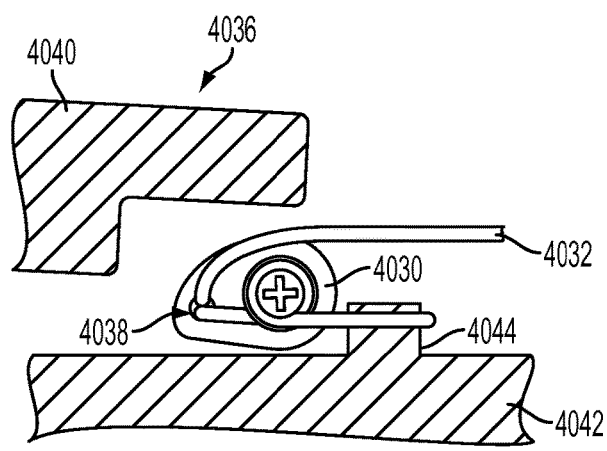
FIG. 13 is a side, partially cross-sectional view of a portion of the device of FIG. 12, the end effector being in an open position.

FIG. 12 and FIG. 13 illustrate an alternate embodiment of a closure mechanism 4030 in the form of a lobe cam that can be configured and used similar to the closure mechanism 4000 of FIG. 9. In this illustrated embodiment, the lobe cam 4030 can be biased to a second position, shown in FIG. 13, corresponding to an end effector 4036 being in an open position, e.g., first and second jaws 4042, 4040 jaws thereof being open. A spring 4038 coupled to the lobe cam 4030 can provide a biasing force that biases the lobe cam 4030 to the second position. The surgical device can include a support member 4044 configured to couple to the spring 4038. An actuator 4032, e.g., a cable, can be configured to be pulled in a proximal direction 4034 to counteract the bias and move the lobe cam 4030 from the second position to a first position, shown in FIG. 12, corresponding to the end effector 4036 being in a closed position.

Figure 14:
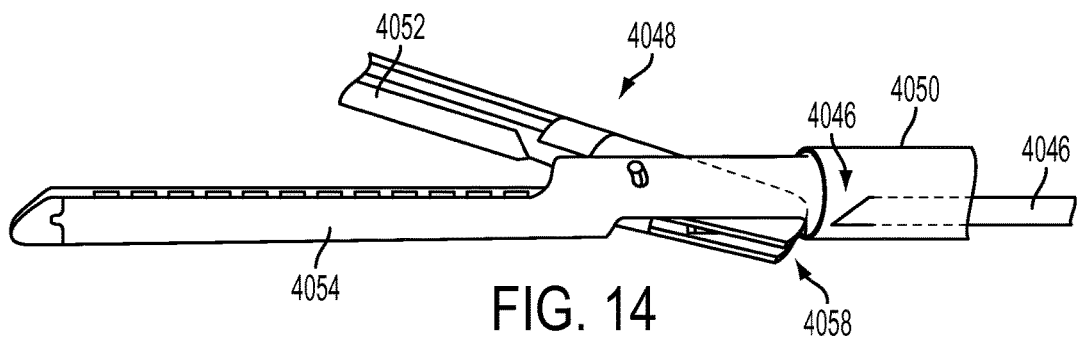
FIG. 14 is a side, partially transparent view of one embodiment of a surgical device including an end effector and a closure mechanism in the form of a wedge, the end effector being in an open position.
Figure 15:
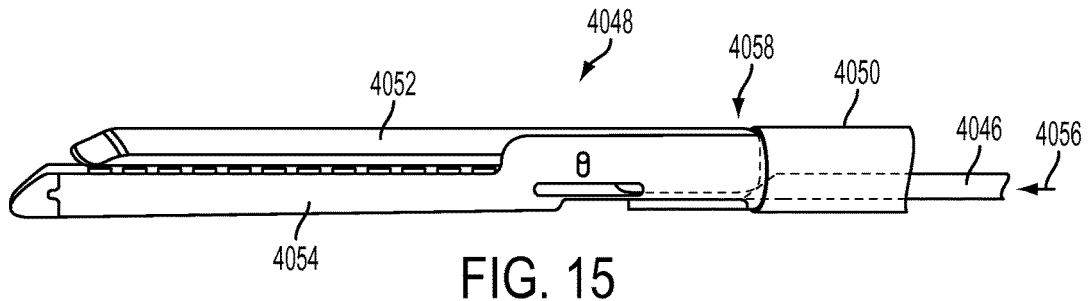
FIG. 15 is a side, partially transparent view of the device of FIG. 14, the end effector in an intermediate position between open position and a closed position.
Figure 16:
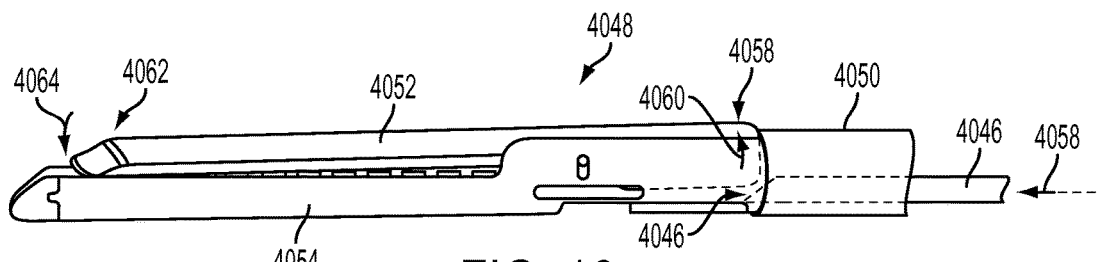
FIG. 16 is a side, partially transparent view of the device of FIG. 15, the end effector being in the closed position.

In some embodiments, a surgical device can include a closure mechanism in the form of a wedge. FIG. 14, FIG. 15, and FIG. 16 illustrate one embodiment of a surgical device that includes a closure mechanism 4046 in the form of a wedge. In general, the wedge 4046 can be configured to improve closing of the device's end effector 4048 and clamping of tissue by the end effector 4048. The end effector 4048 can be coupled to a distal end of the device's elongate shaft 4050, and can include an upper jaw 4052 and a bottom jaw 4054. The wedge 4046 can be configured to be pushed in a distal direction 4056 to improve the moment arm.

The wedge 4046 can have a variety of sizes, shapes, and configurations. As in this illustrated embodiment, the wedge 4046 can be configured to be slidably movable within an inner lumen of the shaft 4050 and can be configured to engage a proximal end 5058 of the upper jaw 4052, as shown in FIG. 15 and FIG. 16. The wedge 4046 can be configured to be so slidably movable by, e.g., manipulating a handle (not shown) of the device. When the end effector 4048 is in an open position, as shown in FIG. 14, the wedge 4046 can be configured to not apply a force to the upper jaw 4052, such as by not being engaged therewith. When the end effector 4048 is moving from the open portion to a closed position, the wedge 4046 can be advanced in the distal direction 4056 such that a cam surface 4046a of the wedge 4046, e.g., a sloped distal end of the wedge 4046, engages the upper jaw 4052 and applies a force to the proximal end 4058 thereof. By being sloped at the distal end thereof, the wedge 4046 can have a relatively low profile at the distal end, which can help the wedge 4046 fit into the relatively small space available at the end effector 4048 while providing the mechanical advantage of an increased moment arm. As in the illustrated embodiment, the wedge 4046 can be advanced under the upper jaw's proximal end 4058 so as to push upward thereon. As the end effector 4048 continues closing, the wedge 4046 can continue applying the force to the upper jaw's proximal end 4058. When the end effector 4048 is in the closed position, as shown in FIG. 16, and similar to the embodiment of FIG. 11, the wedge 4046 can continue applying the force to the upper jaw 4052, which can increase a clamping force of the end effector 4048 by forcing the upper jaw's proximal end in an upward direction 4060, thereby forcing the upper jaw's distal end 4062 in a downward direction 4064 toward the bottom jaw 4054. The upper and bottom jaws 4052, 4054 can be more rigid mechanically in the closed position due to the presence of the wedge 4046. An end reaction force when the end effector 4048 is in the closed position can be in a direction 4064 that is substantially perpendicular to a longitudinal axis of the shaft 4050 along which the wedge 4046 extends. When the end effector 4048 moves from the closed position to the open position, the wedge 4046 can move from the second position back to the first position.

In some embodiments, a surgical device can include a closure mechanism in the form of a two-bar linkage. FIG. 17, FIG. 18, FIG. 19, and FIG. 20 illustrate one embodiment of a surgical device that includes a closure mechanism 4066 in the form of a two-bar linkage. In general, the two-bar linkage 4066 can be configured to improve closing of the device's end effector 4068 and clamping of tissue by the end effector 4068. The end effector 4068 can be coupled to a distal end of the device's elongate shaft 4070, and can include an upper jaw 4072 and a bottom jaw 4074. The two-bar linkage 4066 can be configured to be pulled in a proximal direction 4076 to improve the moment arm.

The two-bar linkage 4066 can have a variety of sizes, shapes, and configurations. As in this illustrated embodiment, the two-bar linkage 4066 can include a first or proximal bar 4078 and a second or distal bar 4080. The first bar 4078 can be coupled to an actuation shaft 4086 slidably disposed along the shaft 4070, e.g., slidably disposed within an inner lumen of the shaft 4070, and actuatable via manipulation of the device's handle (not shown). In some embodiments, the first bar 4078 can be directed manipulated via the handle. The second bar 4080 can be coupled to the first bar 4078, such as at a pivot point 4084, and can be configured to be movable relative thereto, e.g., by pivoting at the pivot point 4084. The second bar 4080 can also be operatively connected to the upper jaw 4072. The second bar 4080 can have a pin 4076 formed thereon. The pin 4076 can be slidably disposed within a slot 4082 formed in the bottom jaw 4074. The pin 4076 can define a pivot point about which the end effector 4068 opens and closes.

Figure 17:
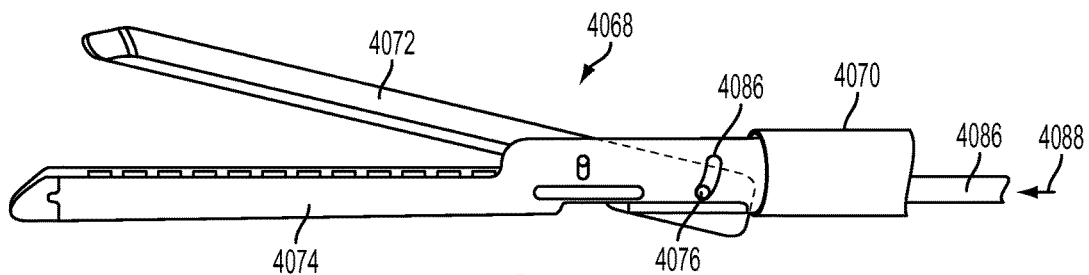
FIG. 17 is a side view of one embodiment of a surgical device including an end effector and a closure mechanism in the form of a two-bar linkage, the end effector being in an open position.
Figure 18:
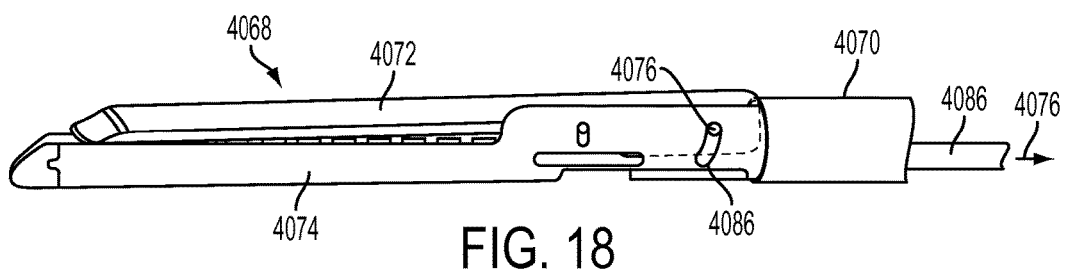
FIG. 18 is a side view of the device of FIG. 17, the end effector being in a closed position.
Figure 19:
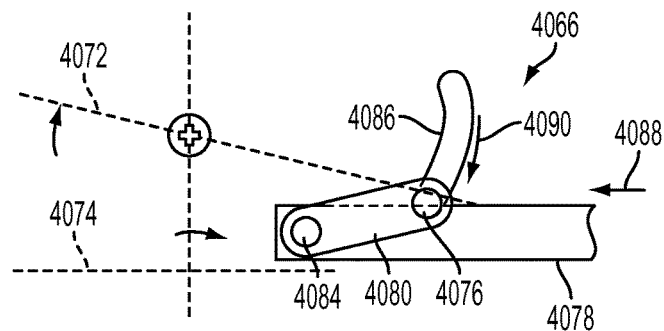
FIG. 19 is a side, partially schematic view of a portion of the device of FIG. 17.
Figure 20:
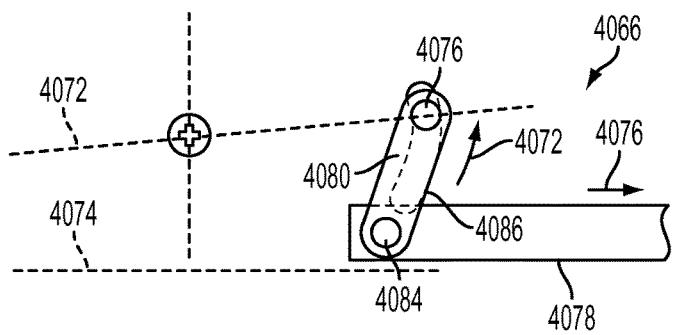
FIG. 20 is a side, partially schematic view of a portion of the device of FIG. 18.

The actuation shaft 4086 and the first bar 4078 coupled thereto can be slidably movable in a distal direction 4088, as shown in FIG. 17 and FIG. 19, and in the proximal direction 4076, as shown in FIG. 18 and FIG. 20. In response to the actuation shaft 4086 and the first bar 4078 moving in the distal direction 4088, the second bar 4080 can move in a downward direction 4090 such that the pin 4076 slides in the downward direction 4090 within the slot 4086, thereby urging the end effector 4068 toward the open position. In response to the actuation shaft 4086 and the first bar 4078 moving in the proximal direction 4076, the second bar 4080 can move in an upward direction 4092 such that the pin 4076 slides in the upward direction 4092 within the slot 4086, thereby urging the end effector 4068 toward the closed position. The upper and bottom jaws 4072, 4074 can be more rigid mechanically in the closed position due to the presence of the two-bar linkage 4066. An end reaction force when the end effector 4068 is in the closed position can be in the downward direction 4090 that is substantially perpendicular to a longitudinal axis of the shaft 4070 along which the actuation shaft 4086 and the first bar 4078 extend.

Figure 21:
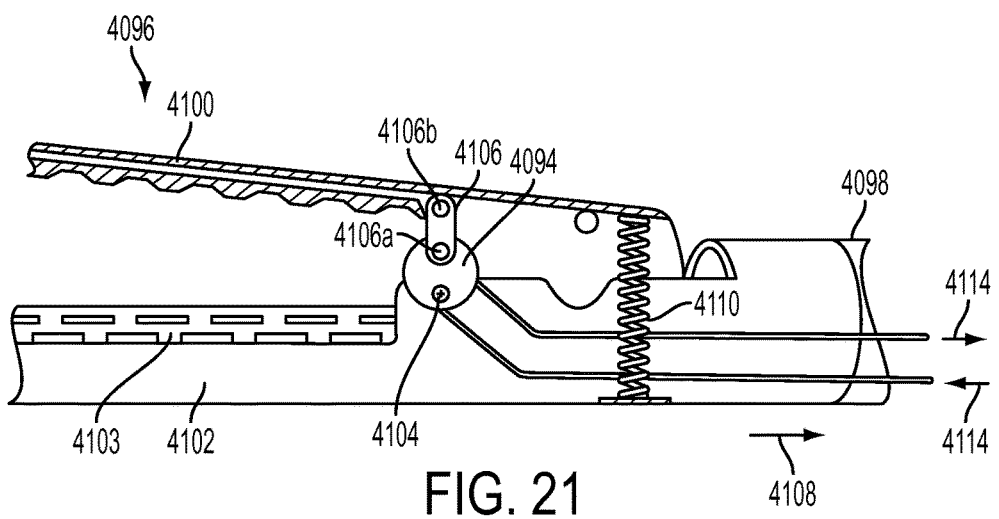
FIG. 21 is a side, partially transparent view of one embodiment of a surgical device including an end effector and a closure mechanism in the form of a rotating element, the end effector being in an open position.
Figure 22:
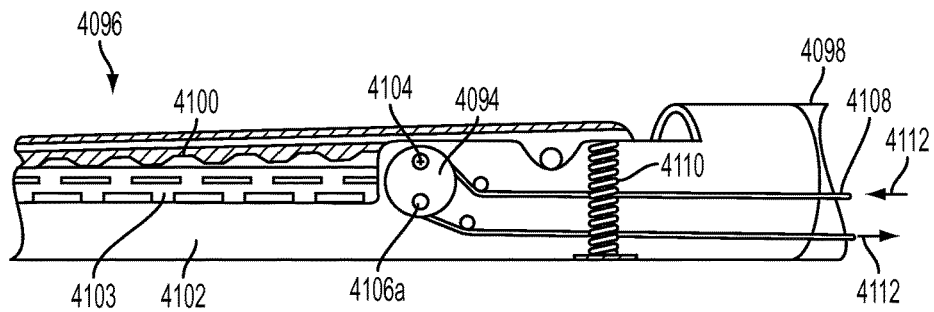
FIG. 22 is a side, partially transparent view of the device of FIG. 21, the end effector being in a closed position.

In some embodiments, a surgical device can include a closure mechanism in the form of a rotating element. FIG. 21 and FIG. 22 illustrate one embodiment of a surgical device that includes a closure mechanism 4094 in the form of a rotating element. In general, the rotating element 4094 can be configured to improve closing of the device's end effector 4096 and clamping of tissue by the end effector 4096. The end effector 4096 can be coupled to a distal end of the device's elongate shaft 4098, and can include an upper jaw 4100 and a bottom jaw 4102. A cartridge 4103 can be seated in the bottom jaw 4102, as shown in this illustrated embodiment. The rotating element 4094 can be configured to rotate to improve the moment arm.

The rotating element 4094 can have a variety of sizes, shapes, and configurations. As in this illustrated embodiment, the rotating element 4094 can include a wheel attached to the bottom jaw 4102 at a fixed point 4104 and attached to the upper jaw 4100 via a link bar 4106. The link bar 4106 can have one end 4106a attached to the wheel 4094 and an opposite end 4106b attached to the upper jaw 4100. The wheel 4094 can be coupled to an actuator 4108 configured to cause rotation of the wheel 4094 at the fixed point 4014. The actuator 4108 can be configured to be actuated via the device's handle (not shown) and can extend along the shaft 4098, as in tis illustrated embodiment. The actuator 4108 can have a variety of sizes, shapes, and configurations. As in this illustrated embodiment, the actuator 4108 can include a cable.

The device can include a bias element 4110, e.g., a spring, configured to bias the end effector 4096 to an open position, shown in FIG. 21. As shown in FIG. 22, in response to the actuator 4108 being moved in a first direction 4112, e.g., counterclockwise, the wheel 4094 can be configured to rotate in the first direction 4112 about the fixed point 4104, thereby causing the ends 4106a, 4106b of the link 4106 to move and the upper jaw 4100 to move toward the bottom jaw 4102. The rotation of the wheel 4094 in the first direction 4112 can thus move the end effector 4096 to the closed position. The movement of the actuator 4108 in the first direction 4112 can overcome the bias force provided by the spring 4110 to allow the end effector 4096 to close.

Similarly, as shown in FIG. 21, in response to the actuator 4108 being moved in a second direction 4114, e.g., clockwise, that is opposite to the first direction 4112, the wheel 4094 can be configured to rotate in the second direction 4114 about the fixed point 4104, thereby causing the ends 4106a, 4106b of the link 4106 to move and the upper jaw 4100 to move away from bottom jaw 4102. The rotation of the wheel 4094 in the second direction 4114 can thus move the end effector 4096 to the open position. The bias force provided by the spring 4110 can facilitate the opening of the end effector 4096.

FIG. 23, FIG. 24, FIG. 25, and FIG. 26 illustrate another embodiment of a surgical device that includes a closure mechanism in the form of a rotating element. In this illustrated embodiment, the rotating element includes a plurality of rotating elements 4116a, 4116b, e.g., rotating wheels. The rotating wheels 4116a, 4116b can generally be configured and used similar to the above-mentioned wheel 4094 and can be coupled to and actuated by first and second actuators 4130a, 4130b, respectively. By including a second wheel 4116b, motions of the wheels 4116a, 4116b can be timed to effect various types of end effector closures. Closure of the device's end effector 4122 can thus be selectively controlled at a user's discretion. In general, the wheels 4116a, 4116b can allow the end effector 4122 to be selectively closed in parallel fashion, closed distal end first, and closed proximal end first.

Figure 23:
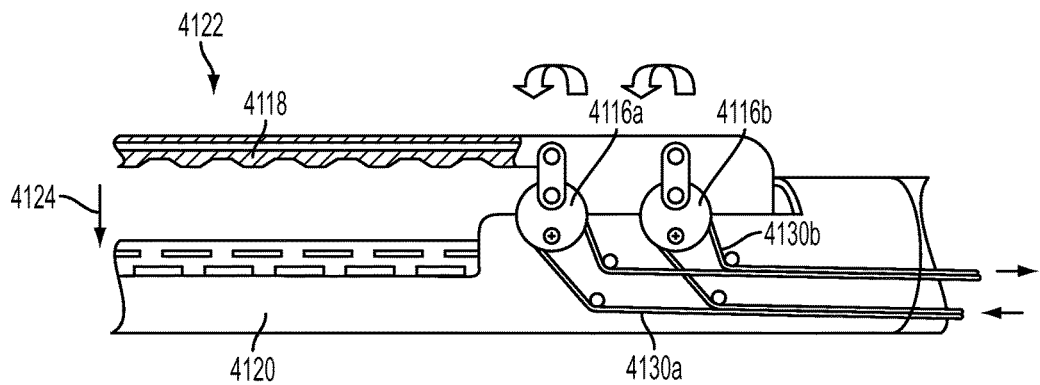
FIG. 23 is a side, partially transparent view of another embodiment of a surgical device including an end effector and a closure mechanism in the form of a rotating element, the end effector being in an open position.
Figure 24:
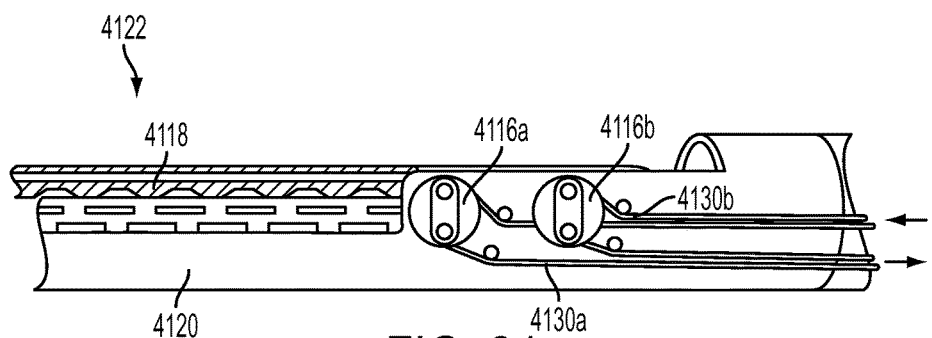
FIG. 24 is a side, partially transparent view of the device of FIG. 23, the end effector being in a closed position.

By including a second wheel 4116b, motions of the wheels 4116a, 4116b can be timed so that they can cause the end effector 4122 to which the wheels 4116a, 4116b are attached to close in a parallel fashion, as shown in FIG. 23 and FIG. 24. In other words, an upper jaw 4118 of the end effector 4112 can move in a downward direction 4124 toward a bottom jaw 4120 of the end effector 4122, as opposed to the rotational "alligator" type closing of the end effector 4096 coupled to a single wheel 4094.

Figure 25:
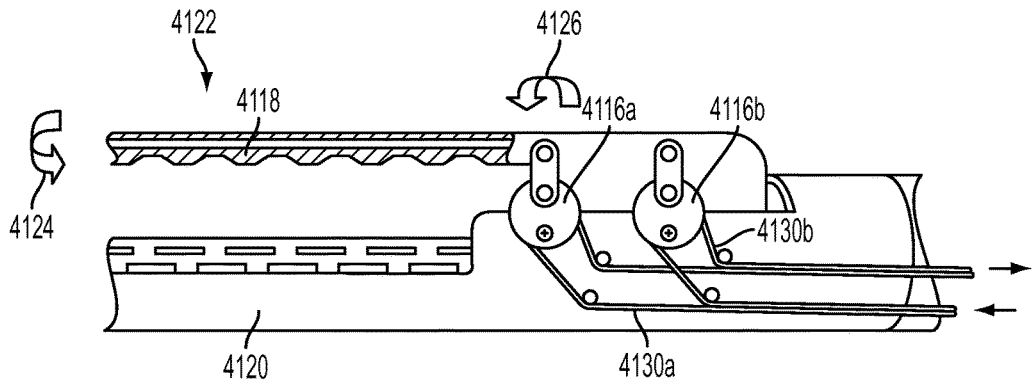
FIG. 25 is a side, partially transparent view of the device of FIG. 23, the rotating element being actuated to cause closing of a distal end of the end effector.

Including a second wheel 4116b can allow the motions of the wheels 4116a, 4116b to be timed so that a distal end (not shown) of the end effector 4122 begins closing first, as indicated by an arrow 4124 in FIG. 25, e.g., before movement of the end effector's proximal end. Closing the distal end first can aid with tissue capture between the jaws 4118, 4120. The motions of the wheels 4116a, 4116b can be controlled to first allow distal closure of the end effector 4122 by starting motion of the distal one of the wheels 4116a, as shown by an arrow 4126, before starting motion of the proximal one of the wheels 4116b.

Figure 26:
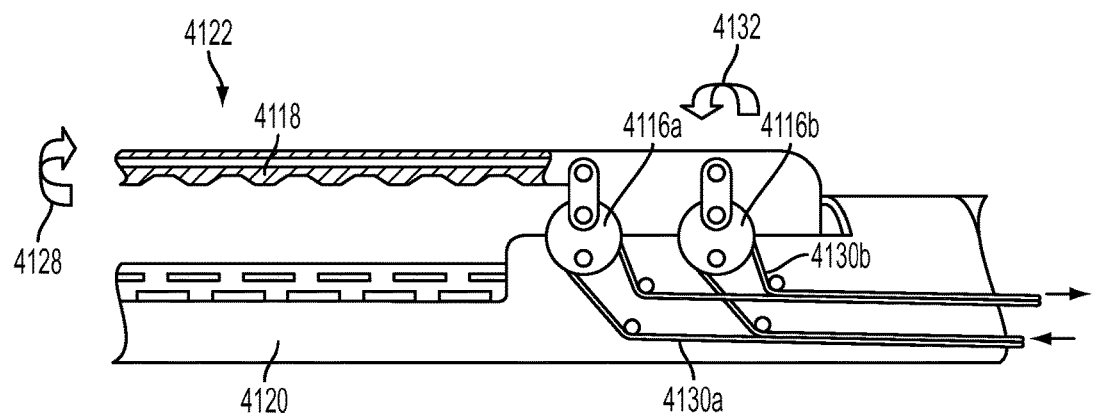
FIG. 26 is a side, partially transparent view of the device of FIG. 23, the rotating element being actuated to cause closing of a proximal end of the end effector.

Including a second wheel 4116b can allow the motions of the wheels 4116a, 4116b to be timed so that the end effector 4112 closes in an "alligator" type fashion by beginning to close the proximal end of the end effector 4122 before beginning to close the distal end of the end effector 4122, as shown in FIG. 26. The motions of the wheels 4116a, 4116b can be controlled to first allow proximal closure of the end effector 4122 by starting motion of the proximal one of the wheels 4116b, as shown by an arrow 4132, before starting motion of the distal one of the wheels 4116a.

Figure 27:
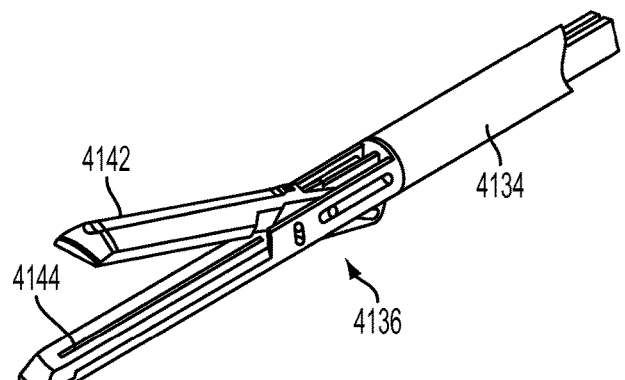
FIG. 27 is a perspective view of one embodiment of a surgical device including an end effector and a closure mechanism in the form of a closure tube, the end effector being in an open position.
Figure 28:
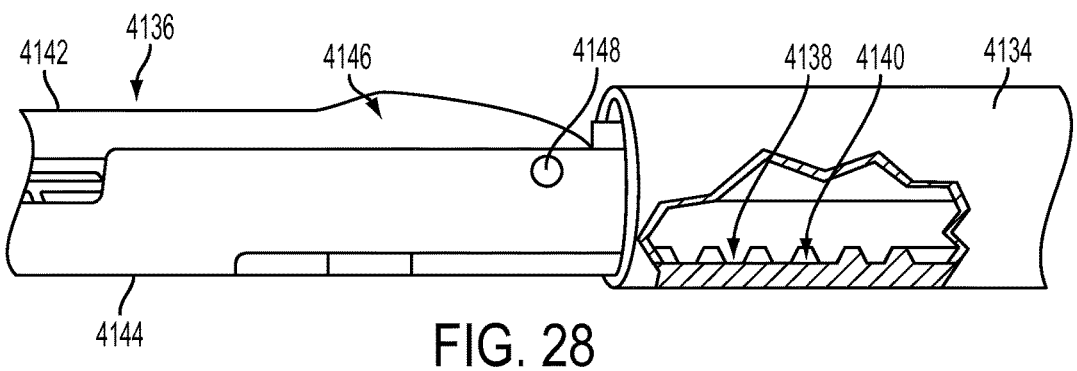
FIG. 28 is a side, partially transparent view of the device of FIG. 27.
Figure 29:
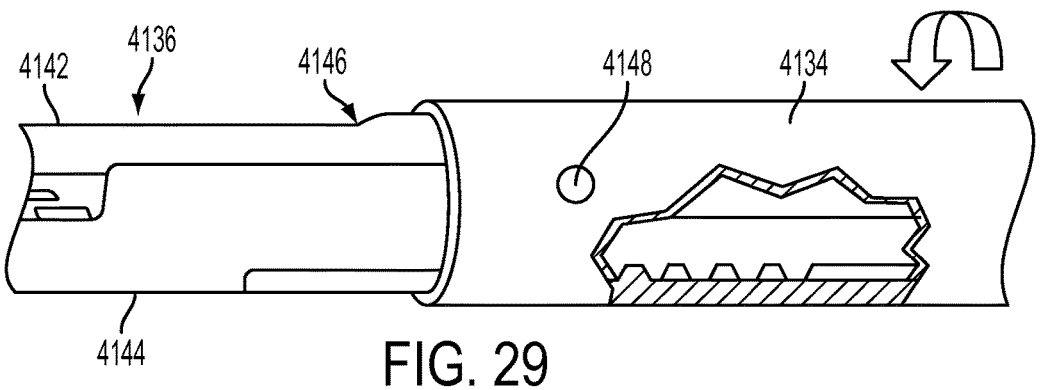
FIG. 29 is a side, partially transparent view of the device of FIG. 27, the end effector being in a closed position.
Figure 30:
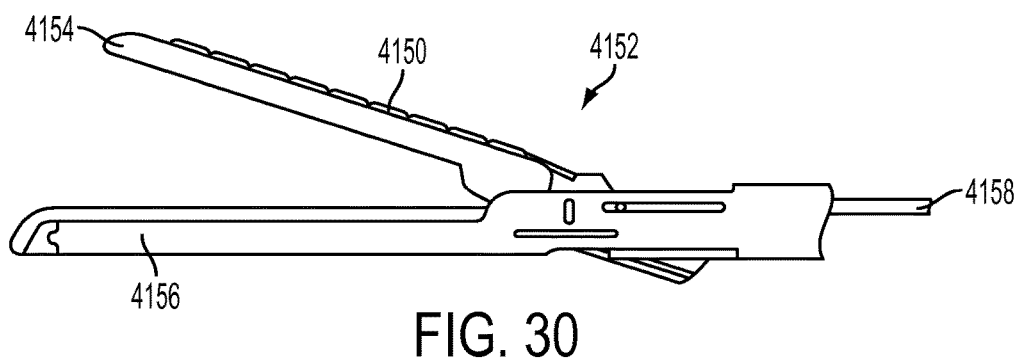
FIG. 30 is a side view of one embodiment of a surgical device including an end effector and a closure mechanism in the form of a truss, the end effector being in an open position and the truss being in a collapsed position.

In some embodiments, a surgical device can include a closure mechanism in the form of a closure tube. FIG. 27, FIG. 28, and FIG. 29 illustrate one embodiment of a surgical device that includes a closure mechanism 4134 in the form of a closure tube. In general, the closure tube 4134 can be configured to rotate to provide increased moment arm to the device's end effector 4136.

The closure tube 4134 can have a variety of sizes, shapes, and configurations, and can be configured to move longitudinally in a variety of ways. As in the illustrated embodiment, the closure tube 4134 can include an internal thread 4138 matable with a corresponding thread 4140 on a stationary one of the end effector's upper and bottom jaws 4142, 4144, e.g., the bottom jaw 4144. The closure tube 4134 can be configured to rotate about a longitudinal axis thereof so as to threadably move the end effector 4136 proximally or distally, depending on a direction of the closure tube's rotation. The internal threads 4138, 4140 can have a consistent size, e.g., have consistent leads therealong, which can allow the end effector 4136 to move longitudinally at a constant rate. Alternatively, as in the illustrated embodiment, the internal threads 4138, 4140 can have a variable size, e.g., have varying leads therealong, which can allow the end effector 4136 to move longitudinally at a variable rate. In this way, the end effector 4136 can be closed at a first rate, e.g., by having larger leads or coarser proximal threads 4138, 4140, and then close at a second, slower rate, e.g., by having smaller leads or finer distal threads 4138, 4140, so as to provide a higher force when the closure tube 4134 is rotating at the second, slower rate so as to provide a greater mechanical advantage.

In response to the closure tube's rotation, the end effector 4136 can be proximally advanced into the closure tube 4136 when closing the end effector 4136, and the end effector 4136 can be distally advanced out of the closure tube 4136 when opening the end effector 4136. A pivot point 4148 about which the end effector 4136 opens and closes, e.g., about which the upper jaw 4142 moves relative to the bottom jaw 4144, can be configured to move in and out of the closure tube 4134. In general, the more proximally located the pivot point 4148, the more force that can be applied to the end effector 4136 to effect its closure and clamping.

The closure tube 4134 can be configured to rotate any number of degrees to fully move the end effector 4136 between the open and closed positions. In an exemplary embodiment, the closure tube 4134 can rotate at least 360°, e.g., one full 360° rotation, three full 360° rotations, five full 360° rotations, six full 360° rotations, etc.

The closure tube 4136 can be configured to be moved longitudinally in a variety of ways. For example, the device can include an actuator (not shown), e.g., a rotatable knob, a movable lever, a rack/pinion mechanism, etc., manipulatable at a handle (not shown) of the device that can be configured to be manipulated to effect movement of the closure tube 4136. For another example, the closure tube 4136 can be configured to rotate in response to an actuator, e.g., a firing trigger, etc., configured to be manipulated to fire fasteners from the device. For yet another example, the rotation of the closure tube 4136 can be configured to be motor-powered. For another example, the closure tube 4136 can be configured to be manually rotated by hand.

The end effector 4136 can include a protruding lobe 4146 extending radially outward therefrom. The protruding lobe 4146 can be configured to increase a force exerted by the closure tube 4134 on the end effector 4136 when the closure tube 4134 engages the protruding lobe 4146, e.g., when the protruding lobe 4146 is at least partially disposed within the tube 4134. FIG. 27 and FIG. 28 show the protruding lobe 4146 outside the closure tube 4134, and FIG. 29 shows the protruding lobe 4146 partially disposed within the closure tube 4134.

In some embodiments, a surgical device can include a closure mechanism in the form of a truss. FIG. 30, FIG. 31, FIG. 32, FIG. 33, and FIG. 34 illustrate one embodiment of a surgical device that includes a closure mechanism 4150 in the form of a truss. In general, the truss 4150 can be configured to improve closing of the device's end effector 4152 and clamping of tissue by the end effector 4152. The smaller an end effector 4152, e.g., the smaller the end effector's diameter, the less bending stiffness the end effector 4152 has, and the more likely the end effector 4152 is to bend and reduce the closure and clamping effectiveness of the end effector 4152. The truss 4150 can be configured to provide increased being stiffness and, thus, make the end effector 4152 less likely to bend, even if the end effector 4152 is small.

The truss 4150 can have a variety of sizes, shapes, and configurations. The truss 4150 can be configured to increase a size of the end effector 4152, e.g., a size of one of the upper and bottom jaws 4154, 4156 thereof, which can increase structural strength the end effector 4152, e.g., by increasing a rigidity of the end effector 4152. This increased structural strength of the end effector 4152 can allow the end effector 4152 to more forcefully close and clamp when the truss 4150 is deployed, e.g., is expanded. In an exemplary embodiment, the truss 4150 can be configured to move between a collapsed position and an expanded position. In the collapsed position, shown in FIG. 30 and FIG. 33 (with the end effector 4152 in solid lines), the end effector 4152 can have a first size and a first strength. As in this illustrated embodiment, the truss 4150 in the collapsed position can be configured to be disposed within one of the jaws 4154, 4156, e.g., the upper jaw 4154. In the expanded position, shown in FIG. 31, FIG. 32, FIG. 33 (with the end effector 4152 in dotted lines), and FIG. 34, the end effector 4152 can have a second size that is greater than the first size and a second strength that is greater than the first strength. As in this illustrated embodiment, the truss 4150 in the expanded position can be configured to extend outward from the one of the jaws 4154, 4156 in which the truss 4150 is disposed when in the collapsed position. The truss 4150 being movable between the collapsed and expanded configurations can allow the device to be advanced into a patient's body with a first, smaller size, e.g., with the truss 4150 in the collapsed position, which can facilitate use of the device in a minimally invasive surgical procedure.

Figure 31:
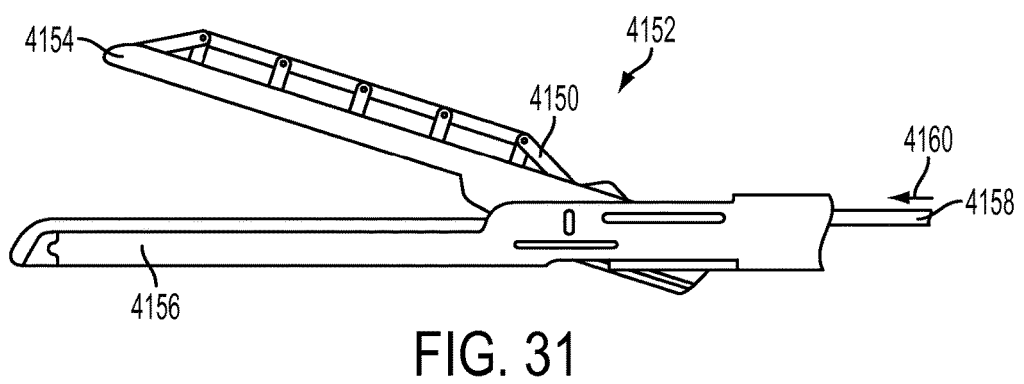
FIG. 31 is a side view of the device of FIG. 30, the truss being in an expanded position.
Figure 32:
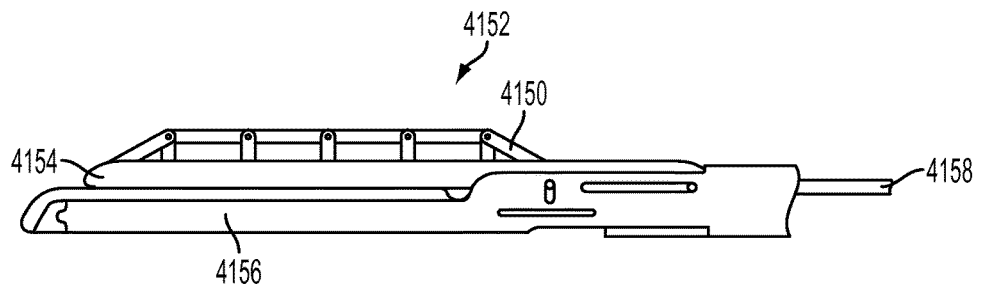
FIG. 32 is a side view of the device of FIG. 31, the end effector being in a closed position.
Figure 33:
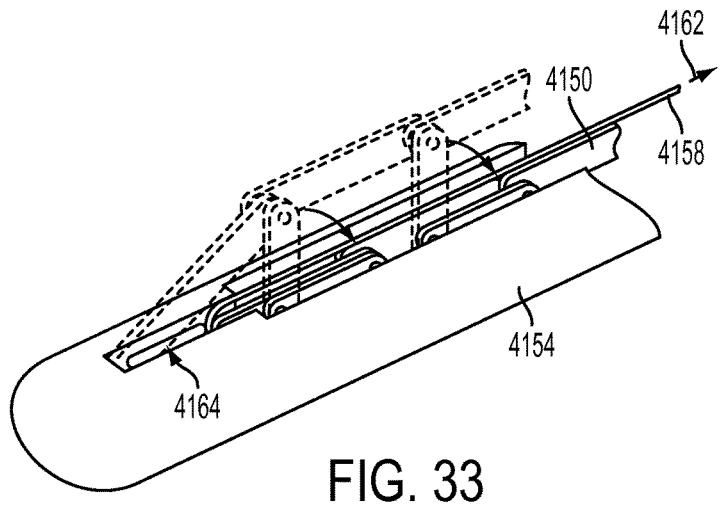
FIG. 33 is a perspective view of a portion of the device of FIG. 30.
Figure 34:
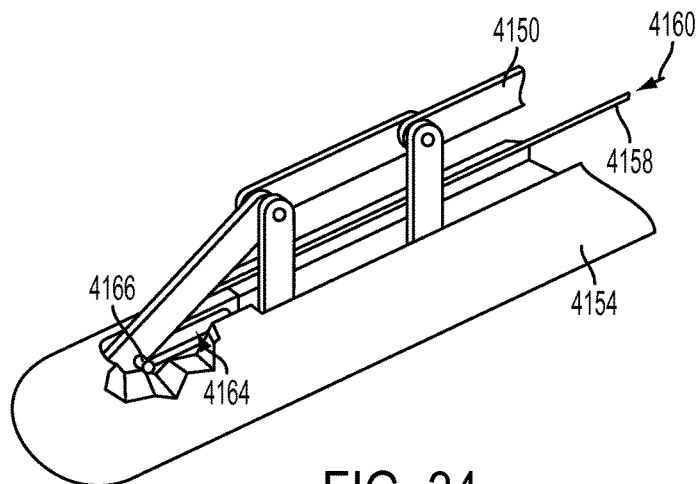
FIG. 34 is a perspective view of a portion of the device of FIG. 31.
Figure 35:
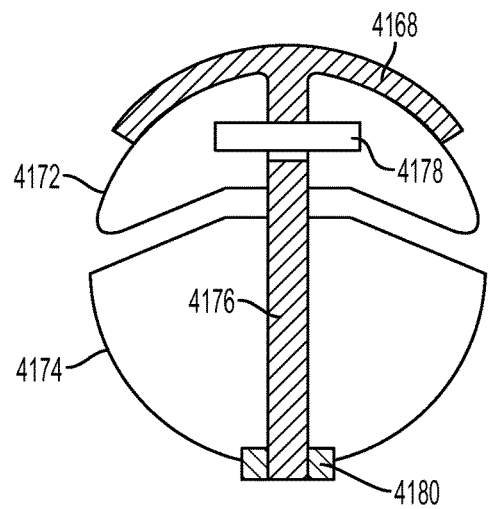
FIG. 35 is a cross-sectional front end view of one embodiment of a surgical device including an end effector and a closure mechanism in the form of an external compression member.
Figure 36:
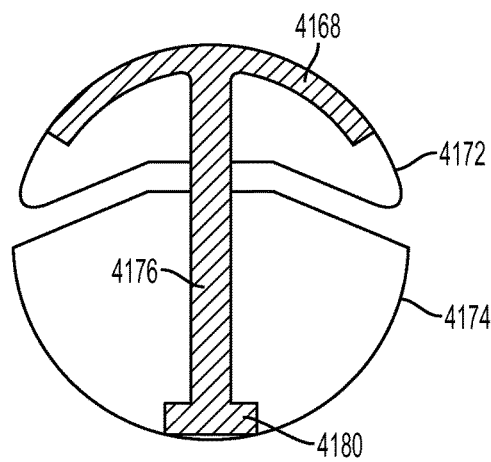
FIG. 36 is cross-sectional back end view of the device of FIG. 35.
Figure 37:
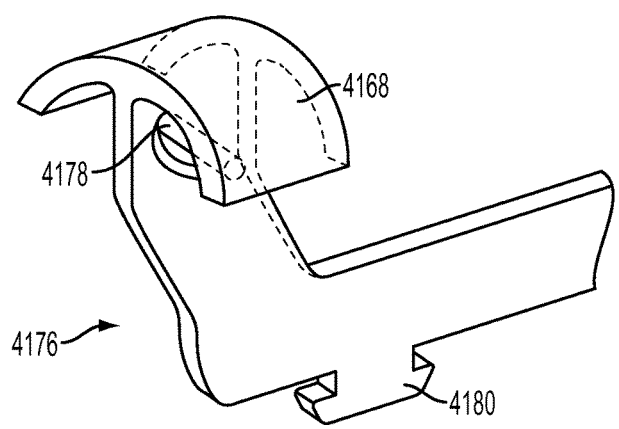
FIG. 37 is a perspective view of the external compression member of FIG. 35.

The truss 4150 can be configured to move between the expanded and collapsed positions in a variety of ways. The device can include an actuator 4158, e.g., a rod, a cable, etc., configured to be manipulated at a handle (not shown) of the device to selectively collapse and expand the truss 4150. In this illustrated embodiment, the actuator 4158 includes a cable. In response to movement of the actuator 4158 in a distal direction 4160, as shown in FIG. 31 and FIG. 34, the truss 4150 can be configured to move from the collapsed position to the expanded position. In response to movement of the actuator 4158 in a proximal direction 4162, as shown in FIG. 33, the truss 4150 can be configured to move from the expanded position to the collapsed position. In other embodiments, proximal movement of an actuator can cause a truss to move from a collapsed position to an expanded position, and distal movement of the actuator can cause the truss to move from the expanded position to the collapsed position.

As in this illustrated embodiment, the truss 4150 can include a plurality of movable links connected together. The truss 4150 includes eight movable links in this illustrated embodiment, but a truss can include another number of movable links.

The end effector 4152 can include a slot 4164 formed therein, as shown in FIG. 33 and FIG. 34, in which the truss 4150 can be configured to slide to facilitate movement between the collapsed and expanded positions. The truss

4150 can include a pin 4166 configured to slide within the slot 4164, as shown in FIG. 34. As in this illustrated embodiment, a distal-most one of the movable links can include the pin 4166. The slot 4164 and the pin 4166 can cooperate to facilitate a smooth, controlled transition of the truss 4150 between the collapsed and expanded positions.

In some embodiments, a surgical device can include a closure mechanism in the form of an external compression member. FIG. 35, FIG. 36, FIG. 37, FIG. 38, and FIG. 39 illustrate one embodiment of a surgical device that includes a closure mechanism 4168 in the form of an external compression member. In general, the external compression member 4168 can be configured to improve closing of the device's end effector 4170 and clamping of tissue by the end effector 4170. The end effector 4170 can include an upper jaw 4172 and a bottom jaw 4174. The external compression member 4168 can be configured to translate along the end effector 4170 externally thereto to apply a closing force thereto, thereby improving the moment arm. The external compression member 4168, being external to the end effector 4170, can be configured as an exoskeleton. Being located to the end effector 4170 can allow the external compression member 4168 to help prevent twisting and/or shifting of the end effector 4170 during firing of fasteners from the end effector 4170. By being located external to the end effector 4170, the external compression member 4168 can be positioned radially outward from a longitudinal axis of the end effector 4170, which can allow the external compression member 4168 to provide support and closing force to the end effector 4170, e.g., to the one of the jaws 4172 along whose external surface the external compression member 4168 translates.

The device includes a single external compression member 4168 in this illustrated embodiment, but in some embodiments, a device can include a plurality of external compression members. For example, a first compression member can be configured to translate along a first end effector jaw, and a second compression member can be configured to translate along a second end effector jaw.

The external compression member 4168 can have a variety of sizes, shapes, and configurations. In an exemplary embodiment, the external compression member 4168 can be formed on an I-beam 4176 configured to translate along the end effector 4170, as discussed herein. The I-beam 4176 can thus be configured translate along the end effector 4170 with a portion thereof, e.g., the external compression member 4168, translating outside the end effector 4170. The external compression member 4168 can thus be configured to be actuated in conjunction with actuation of the I-beam 4176, which can make the external compression member 4168 easy for a user to actuate. The external compression member 4168 can be formed on an upper portion of the I-beam 4176, as in this illustrated embodiment, such that the external compression member 4168 can form a "roof" of the I-beam 4176.

The I-beam 4716 can include other features, as will be appreciated by a person skilled in the art, such as a guide pin 4178 configured to translate along the upper jaw 4172, e.g., in a channel formed therein, to facilitate closing of the end effector 4170, and such as a foot 4180 configured to translate along the bottom jaw 4174, e.g., in a longitudinal slot formed therein, to facilitate smooth, controlled translation of the I-beam 4176 through the end effector 4170.

Figure 38:
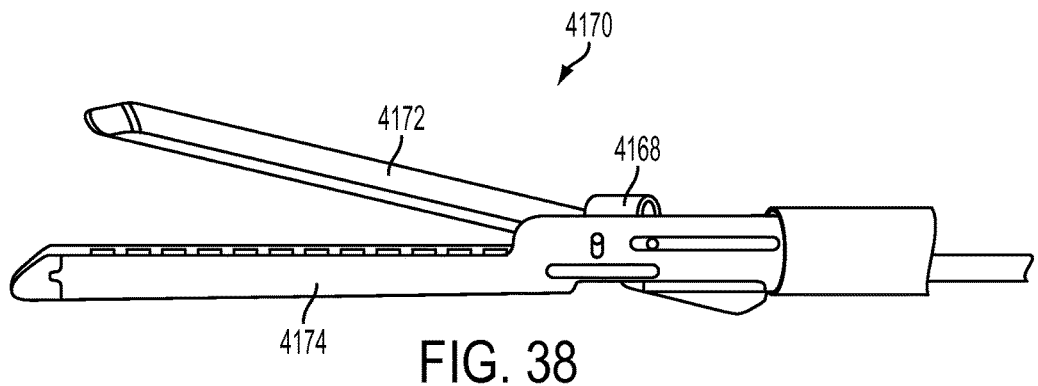
FIG. 38 is a side view of the end effector and the external compression member of FIG. 35, the end effector being in an open position.
Figure 39:
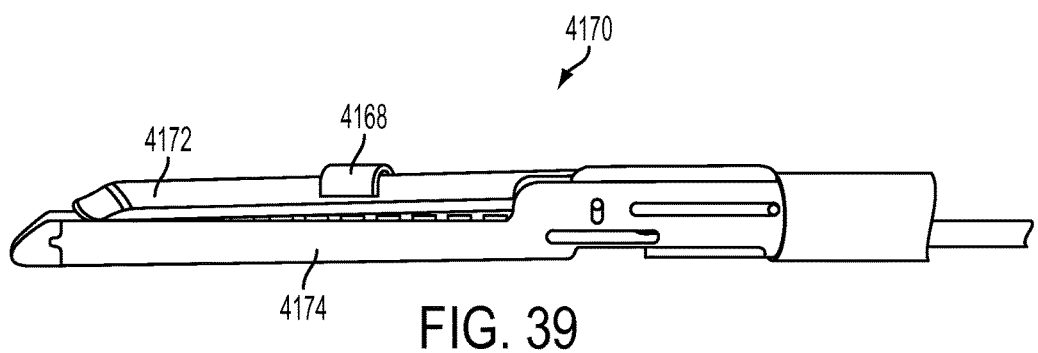
FIG. 39 is a side view of the end effector and the external compression member of FIG. 35, the end effector being in a closed position.

When the end effector 4170 is in an open position, as shown in FIG. 38, the external compression member 4168 can be located adjacent a proximal end of the end effector 4170. As shown in FIG. 39, as the end effector 4170 moves from the open position to a closed position, the external compression member 4168 can translate distally along the end effector 4168 so as to provide a compressive force thereto during firing of fasteners disposed within the end effector 4170, as discussed herein.

Figure 40:
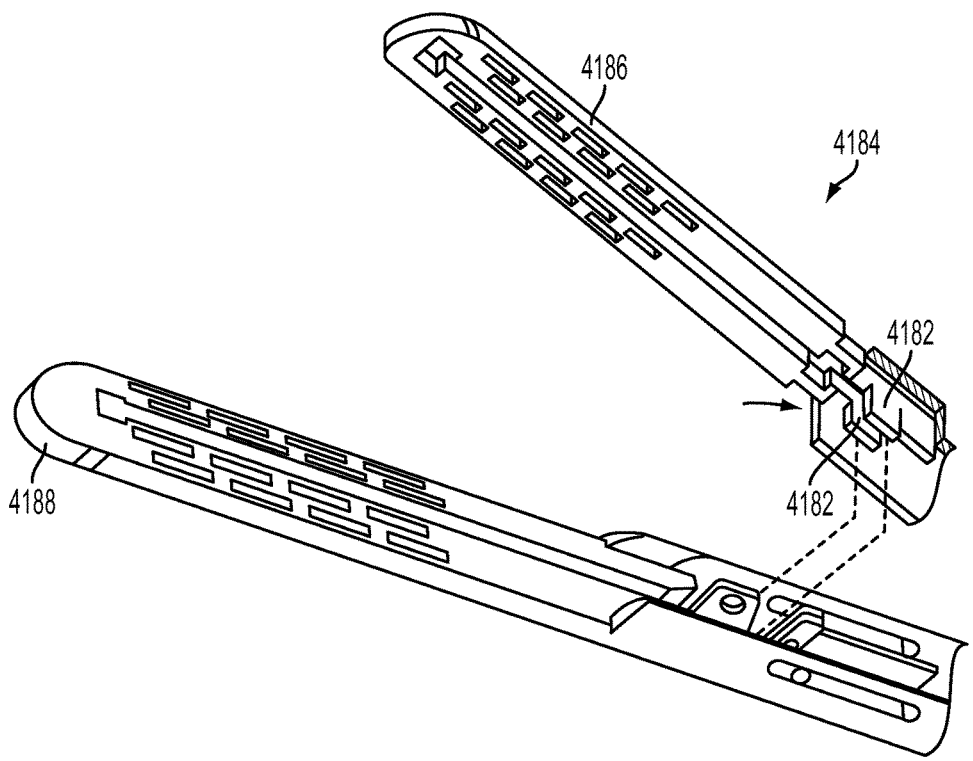
FIG. 40 is an exploded perspective view of one embodiment of a surgical device including an end effector and a closure mechanism in the form of an internal end effector protrusion.
Figure 41:
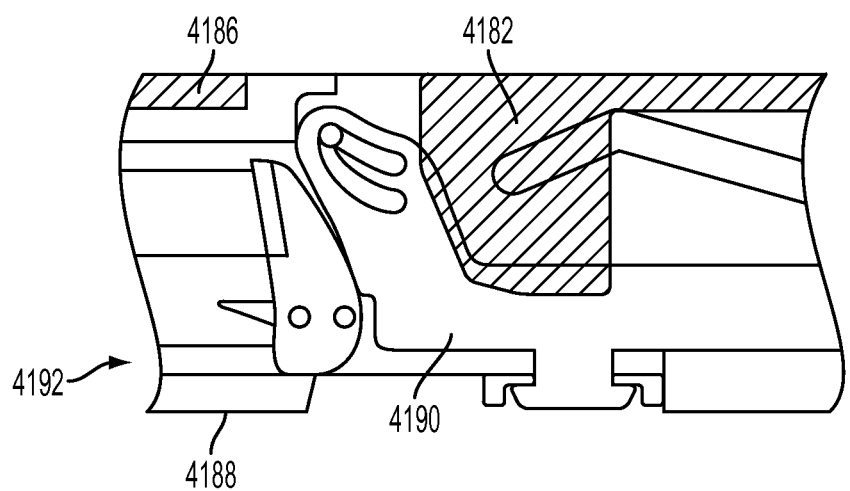
FIG. 41 is a side, cross-sectional view of the end effector and the closure mechanism of FIG. 40.

In some embodiments, a surgical device can include a closure mechanism in the form of an internal end effector protrusion. FIG. 40 and FIG. 41 illustrate one embodiment of a surgical device that includes a closure mechanism 4182 in the form of an internal end effector protrusion. In general, the internal end effector protrusion 4182 can be configured to improve closing of the device's end effector 4184 and clamping of tissue by the end effector 4184. The end effector 4184 can include an upper jaw 4186 and a bottom jaw 4188. The internal end effector protrusion 4182 can be configured to increase stiffness of the end effector 4184 to improve the moment arm.

The internal end effector protrusion 4182 can have a variety of sizes, shapes, and configurations. As in this illustrated embodiment, the internal end effector protrusion 4182 can include one or more support members located adjacent a proximal end of the end effector 4184. By being located near the end effector's proximal end, the closure mechanism 4182 can be configured to provide increased strength to the effector's proximal end, which can increase a moment of inertia of the end effector's proximal end, thereby increasing the moment arm. The closure mechanism 4182 can be formed on the upper jaw 4186, as in this illustrated embodiment, and extend in a direction toward the bottom jaw 4188.

The device in this illustrated embodiment includes two support members 4182, but a device can include another number of lateral support members. The two support members 4182 can be positioned on either side of an I-beam 4190, as shown in FIG. 41, that can be configured to translate through the end effector 4184 and advance a sled 4192 therethrough, as discussed herein. The support members 4182 can thus be configured to help guide and support the I-beam 4190 and/or help prevent buckling of the I-beam 4190 in embodiments in which the I-beam 4190 is flexible.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical fastening device, comprising:
an elongate shaft; and
an end effector coupled to a distal end of the elongate shaft, the end effector including
a cartridge jaw and an anvil pivotally coupled to one another at a pivot point,
a cam pin disposed within a cam slot formed in each of the cartridge jaw and the anvil, the cam pin being slidable within the cam slots to move the anvil and cartridge jaw between a spaced-apart position and a closed position in which the cartridge jaw and the anvil are configured to engage tissue therebetween, and
a closure mechanism proximal to the pivot point, the closure mechanism being in the form of a lobe cam and being positioned adjacent to a proximal-most end of the anvil and being configured to apply a force to the proximal-most end of the anvil to compress tissue engaged between the anvil and the cartridge jaw.

2. The device of claim 1, wherein the closure mechanism comprises the lobe cam that rotates to apply a force to the proximal-most end of the anvil to move the proximal-most end of the anvil away from the cartridge jaw.

3. The device of claim 2, further comprising a cable coupled to the lobe cam and configured to rotate the lobe cam to cause the lobe cam to apply a force to the proximal-most end of the anvil.

4. The device of claim 2, wherein the lobe cam includes a biasing element that biases the lobe cam to a position in which no force is applied to the proximal-most end of the anvil.

5. The device of claim 1, wherein the closure mechanism comprises a wedge configured to apply a force to the proximal-most end of the anvil to move the proximal-most end of the anvil away from the cartridge jaw.

6. The device of claim 5, wherein the wedge is configured to advance distally to apply the force to the proximal-most end of the anvil.

7. The device of claim 5, wherein the wedge is formed on a distal end of a pusher shaft slidably disposed through the elongate shaft.

8. A surgical fastening device, comprising:
a handle;
an elongate shaft extending distally from the handle; and
an end effector coupled to a distal end of the elongate shaft, the end effector including first and second jaws pivotally coupled to one another and movable about a pivot point between an open position and a closed position for engaging tissue;
a lobe cam positioned proximal to the pivot point and between a proximal-most end of each of the first and second jaws, the lobe cam being rotatable to move the proximal-most ends of the first and second jaws apart to thereby move the first and second jaws to the closed position.

9. The device of claim 8, wherein the lobe cam is biased to a position in which the first and second jaws are in the open position, and rotation of the lobe cam overcomes the bias to move the first and second jaws to the closed position.

10. The device of claim 8, further comprising a cable coupled to the lobe cam and configured to rotate the lobe cam to cause the lobe cam to apply a force to move the first and second jaws to the closed position.

11. The device of claim 8, wherein a distance between the first and second jaws at the pivot point is adjustable.

* * * * *